US007494964B2

(12) United States Patent
Schlingloff et al.

(10) Patent No.: US 7,494,964 B2
(45) Date of Patent: *Feb. 24, 2009

(54) USE OF METAL COMPLEX COMPOUNDS AS OXIDATION CATALYSTS

(75) Inventors: Gunther Schlingloff, Riehen (CH); Torsten Wieprecht, Schopfheim (DE); Frank Bachmann, Freiburg (DE); Josef Dannacher, Basel (CH); Marie-Josée Dubs, Wittersdorf (FR); Menno Hazenkamp, Riehen (CH); Uwe Heinz, Saarlouis (DE); Markus Frey, Rheinfelden (CH); Albert Schneider, Grenzach-Wyhlen (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/520,841

(22) PCT Filed: Jul. 3, 2003

(86) PCT No.: PCT/EP03/07121

§ 371 (c)(1),
(2), (4) Date: Sep. 15, 2005

(87) PCT Pub. No.: WO2004/007657

PCT Pub. Date: Jan. 22, 2004

(65) Prior Publication Data

US 2006/0100123 A1    May 11, 2006

(30) Foreign Application Priority Data

Jul. 11, 2002    (EP) ................... 02405591

(51) Int. Cl.
*C11D 7/32* (2006.01)
*C11D 7/38* (2006.01)
*C11D 7/54* (2006.01)

(52) U.S. Cl. .................. 510/311; 510/372; 510/376; 510/500; 510/504; 510/505; 8/111; 8/137; 252/186.33; 502/200; 502/324; 502/325

(58) Field of Classification Search .............. None
See application file for complete search history.

(56) References Cited

U.S. PATENT DOCUMENTS

| 4,960,895 A | 10/1990 | Ohkawa ................ 546/257 |
| 7,161,005 B2 * | 1/2007 | Schlingloff et al. ......... 546/2 |

FOREIGN PATENT DOCUMENTS

| EP | 1217056 | 6/2002 |
| FR | 2677766 | 12/1992 |
| WO | 01/46368 | 6/2001 |
| WO | 02/088289 | 11/2002 |

OTHER PUBLICATIONS

E. C. Constable et al., Crossfire Beilstein, Accession No. 3613386, Oct. 23, 1991.
G. Lowe et al., Crossfire Beilstein, Accession No. 8321073, Mar. 7, 2000.

* cited by examiner

*Primary Examiner*—Gregory R Del Cotto
(74) *Attorney, Agent, or Firm*—Mervin G. Wood

(57) ABSTRACT

The present invention relates to the use of metal complex compounds which have terpyridine ligands and contain at least one quaternized nitrogen atom as oxidation catalysts. The present invention relates also to formulations comprising such metal complex compounds, to novel metal complex compounds and to novel ligands.

20 Claims, No Drawings

USE OF METAL COMPLEX COMPOUNDS AS OXIDATION CATALYSTS

The present invention relates to the use of metal complex compounds which have terpyridine ligands and contain at least one quaternized nitrogen atom as oxidation catalysts. The present invention relates also to formulations comprising such metal complex compounds, to novel metal complex compounds and to novel ligands.

The metal complex compounds are used especially for improving the action of peroxides, for example in the treatment of textile material, without at the same time causing any appreciable damage to fibres and dyeings.

Peroxide-containing bleaching agents have been used in washing and cleaning processes for some time. They have an excellent action at a liquor temperature of 90° C. and above, but their performance noticeably decreases with lower temperatures. It is known that various transition metal ions, added in the form of suitable salts, or coordination compounds containing such cations, activate $H_2O_2$. In that way it is possible to increase the bleaching action of $H_2O_2$, or of precursors that release $H_2O_2$, or of other peroxo compounds, the bleaching action of which is unsatisfactory at lower temperatures. Particularly significant for practical purposes are those combinations of transition metal ions and ligands the peroxide activation of which is manifested in an increased tendency towards oxidation in respect of substrates and not only in a catalase-like disproportionation. The latter activation, which tends rather to be undesirable in the present case, could even impair the bleaching effects of $H_2O_2$ and its derivatives which are insufficient at low temperatures.

In respect of $H_2O_2$ activation having effective bleaching action, mononuclear and polynuclear variants of manganese complexes with various ligands, especially with 1,4,7-trimethyl-1,4,7-triazacyclononane and optionally oxygen-containing bridge ligands, are currently regarded as being especially effective. Such catalysts have adequate stability under practical conditions and, with $Mn^{n+}$, contain an ecologically acceptable metal cation, but their use is unfortunately associated with considerable damage to dyes and fibres.

The aim of the present invention was, therefore, to provide improved metal complex catalysts for oxidation processes which fulfil the above demands and, especially, improve the action of peroxide compounds in an extremely wide range of fields of use without giving rise to any appreciable damage.

The invention accordingly relates to the use of metal complex compounds of formula (1)

$$[L_n Me_m X_p]^z Y_q \qquad (1)$$

wherein Me is manganese, titanium, iron, cobalt, nickel or copper,

X is a coordinating or bridging radical, n and m are each independently of the other an integer having a value of from 1 to 8, p is an integer having a value of from 0 to 32, z is the charge of the metal complex, Y is a counter-ion, q=z/(charge Y), and L is a ligand of formula (2)

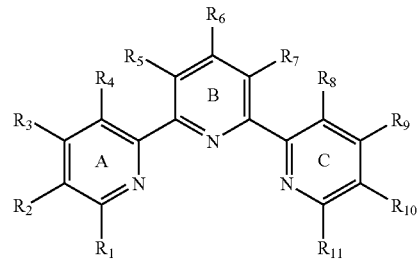

wherein $R_1$, $R_2$, $R_3$, $R_4$, $R_5$, $R_6$, $R_7$, $R_8$, $R_9$, $R_{10}$ and $R_{11}$ are each independently of the others hydrogen; unsubstituted or substituted $C_1$-$C_{18}$alkyl or aryl; cyano; halogen; nitro; —COOR$_{12}$ or —SO$_3$R$_{12}$ wherein R$_{12}$ is in each case hydrogen, a cation or unsubstituted or substituted $C_1$-$C_{18}$alkyl or aryl; —SR$_{13}$, —SO$_2$R$_{13}$ or —OR$_{13}$ wherein R$_{13}$ is in each case hydrogen or unsubstituted or substituted $C_1$-$C_{18}$alkyl or aryl; —NR$_{14}$R$_{15}$; —(C$_1$-C$_6$alkylene)-NR$_{14}$R$_{15}$; —N$^{\oplus}$R$_{14}$R$_{15}$R$_{16}$; —(C$_1$-C$_6$alkylene)-N$^{\oplus}$R$_{14}$R$_{15}$R$_{16}$; —N(R$_{13}$)-(C$_1$-C$_6$alkylene)-NR$_{14}$R$_{15}$; —N[(C$_1$-C$_6$alkylene)-NR$_{14}$R$_{15}$]$_2$; —N(R$_{13}$)—(C$_1$-C$_6$alkylene)-N$^{\oplus}$R$_{14}$R$_{15}$R$_{16}$; —N[(C$_1$-C$_6$alkylene)-N$^{\oplus}$R$_{14}$R$_{15}$R$_{16}$]$_2$; —N(R$_{13}$)—N—R$_{14}$R$_{15}$ or —N(R$_{13}$)—N$^{\oplus}$R$_{14}$R$_{15}$R$_{16}$, wherein R$_{13}$ is as defined above and R$_{14}$, R$_{15}$ and R$_{16}$ are each independently of the other(s) hydrogen or unsubstituted or substituted $C_1$-$C_{18}$alkyl or aryl, or R$_{14}$ and R$_{15}$ together with the nitrogen atom bonding them form an unsubstituted or substituted 5-, 6- or 7-membered ring which may optionally contain further heteroatoms; with the proviso that (i) at least one of the substituents R$_1$—R$_{11}$ contains a quaternized nitrogen atom which is not directly bonded to one of the three pyridine rings A, B or C and that (ii) Y is neither I$^-$ nor Cl$^-$ in the case that Me is Mn(II), R$_1$—R$_5$ and R$_7$—R$_{11}$ are hydrogen and R$_8$ is

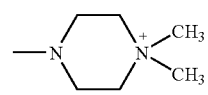

as catalysts for oxidation reactions.

The $C_1$-$C_{18}$alkyl radicals mentioned are generally, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals can be unsubstituted or substituted e.g. by hydroxyl, $C_1$-$C_4$alkoxy, sulfo or by sulfato, especially by hydroxyl. The corresponding unsubstituted alkyl radicals are preferred. Very special preference is given to methyl and ethyl, especially methyl.

Examples of aryl radicals that generally come into consideration are phenyl or naphthyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di$C_1$-$C_4$alkylamino unsubstituted or substituted by hydroxy in the alkyl moiety, N-phenylamino, N-naphthylamino, where the amino groups may be quaternized, phenyl, phenoxy or by naphthoxy. Preferred substituents are $C_1$-$C_4$alkyl, $C_1$-$C_4$alkoxy, phenyl and hydroxy.

Special preference is given to the corresponding phenyl radicals.

The $C_1$-$C_6$alkylene groups mentioned are generally, for example, straight-chain or branched alkylene radicals such as methylene, ethylene, n-propylene or n-butylene. The alkylene radicals mentioned can be unsubstituted or substituted, for example by hydroxyl or $C_1$-$C_4$alkoxy.

Halogen is generally preferably chlorine, bromine or fluorine, special preference being given to chlorine.

Examples of cations that generally come into consideration are alkali metal cations, such as lithium, potassium and especially sodium, alkaline earth metal cations, such as magnesium and calcium, and ammonium cations. The corresponding alkali metal cations, especially sodium, are preferred.

Suitable metal ions for Me are e.g. manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt II-III, nickel II-III and copper II-III, especially iron II-IV.

For the radical X there come into consideration, for example, $CH_3CN$, $H_2O$, F, $Cl^-$, $Br^-$, $HOO^-$, $O_2^{2-}$, $O^{2-}$, $R_{17}COO^-$, $R_{17}O^-$, $LMeO^-$ and $LMeOO^-$, wherein $R_{17}$ is hydrogen, $-SO_3C_1$-$C_4$alkyl or unsubstituted or substituted $C_1$-$C_{18}$akyl or aryl, and $C_1$-$C_{18}$alkyl, aryl, L and Me have the definitions and preferred meanings given hereinabove and hereinbelow. $R_{17}$ is especially preferably hydrogen, $C_1$-$C_4$alkyl; sulfophenyl or phenyl, especially hydrogen.

As counter-ion Y there come into consideration, for example, $R_{17}COO^-$, $ClO_4^-$, $BF_4^-$, $PF_6^-$, $R_{17}SO_3^-$, $R_{17}SO_4^-$; $SO_4^{2-}$, $NO_3^-$, F, $Cl^-$, $Br^-$ and $I^-$, wherein $R_{17}$ is hydrogen or unsubstituted or substituted $C_1$-$C_{18}$alkyl or aryl. $R_{17}$ as $C_1$-$C_{18}$alkyl or aryl has the definitions and preferred meanings given hereinabove and hereinbelow. $R_{17}$ is especially preferably hydrogen, $C_1$-$C_4$alkyl; phenyl or sulfophenyl, especially hydrogen or 4-sulfophenyl. The charge of the counter-ion Y is accordingly preferably 1- or 2-, especially 1-. Y can also be a customary organic counter-Ion, such as citrate, oxalate or tartrate.

n is preferably an integer having a value of from 1 to 4, preferably 1 or 2 and especially 1.

m is preferably an integer having a value of 1 or 2, especially 1.

p is preferably an integer having a value of from 0 to 4, especially 2.

z is preferably an integer having a value of from 8− to 8+, especially from 4− to 4+ and especially preferably from 0 to 4+. z is more especially preferably the number 0.

q is preferably an integer from 0 to 8, especially from 0 to 4 and is especially preferably the number 0.

$R_{12}$ is preferably hydrogen, a cation, $C_1$-$C_{12}$alkyl, or phenyl unsubstituted or substituted as indicated above. $R_{12}$ is especially preferably hydrogen, an alkali metal cation, alkaline earth metal cation or ammonium cation, $C_1$-$C_4$alkyl or phenyl, more especially hydrogen or an alkali metal cation, alkaline earth metal cation or ammonium cation.

$R_{13}$ is preferably hydrogen, $C_1$-$C_{12}$alkyl, or phenyl unsubstituted or substituted as indicated above. $R_{13}$ is especially preferably hydrogen, $C_1$-$C_4$alkyl or phenyl, more especially hydrogen or $C_1$-$C_4$alkyl, preferably hydrogen. Examples of the radical of the formula $-OR_{13}$ that may be mentioned include hydroxyl and $C_1$-$C_4$alkoxy, such as methoxy and especially ethoxy.

When $R_{14}$ and $R_{15}$ together with the nitrogen atom bonding them form a 5-, 6 or 7-membered ring it is preferably an unsubstituted or $C_1$-$C_4$alkyl-substituted pyrrolidine, piperidine, piperazine, morpholine or azepane ring, where the amino groups can optionally be quaternized, preferably the nitrogen atoms which are not directly bonded to one of the three pyridine rings A, B or C being quaternized. The piperazine ring can be substituted by one or two unsubstituted $C_1$-$C_4$alkyl and/or substituted $C_1$-$C_4$alkyl e.g. at the nitrogen atom not bonded to the phenyl radical. In addition, $R_{14}$, $R_{15}$ and $R_{16}$ are preferably hydrogen, unsubstituted or hydroxyl-substituted $C_1$-$C_{12}$alkyl, or phenyl unsubstituted or substituted as indicated above. Special preference is given to hydrogen, unsubstituted or hydroxyl-substituted $C_1$-$C_4$alkyl or phenyl, especially hydrogen or unsubstituted or hydroxyl-substituted $C_1$-$C_4$alkyl, preferably hydrogen.

Preference is given to ligands of formula (2) wherein $R_6$ is not hydrogen.

$R_6$ is preferably $C_1$-$C_{12}$alkyl; phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy; cyano; halogen; nitro; $-COOR_{12}$ or $-SO_3R_{12}$ wherein $R_{12}$ is in each case hydrogen, a cation, $C_1$-$C_{12}$alkyl, or phenyl unsubstituted or substituted as indicated above; $-SR_{13}$, $-SO_2R_{13}$ or $-OR_{13}$ wherein $R_{13}$ is in each case hydrogen, $C_1$-$C_{12}$alkyl, or phenyl unsubstituted or substituted as indicated above; $-NR_{14}R_{15}$; $-(C_1$-$C_6$alkylene)-$NR_{14}R_{15}$; $-NR_{14}R_{15}R_{16}$; $-(C_1$-$C_6$alkylene)-$N^{\oplus}R_{14}R_{15}R_{16}$; $-N(R_{13})-(C_1$-$C_6$alkylene)-$NR_{14}R_{15}$; $-N(R_{13})-(C_1$-$C_6$alkylene)-$N^{\oplus}R_{14}R_{15}R_{16}$; $-N(R_{13})-$N$-R_{14}-R_{15}$ or $-N(R_{13})-N^{\oplus}R_{14}R_{15}R_{16}$, wherein $R_{13}$ can have one of the above meanings and $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form a pyrrolidine, piperidine, piperazine, morpholine or azepane ring which is unsubstituted or substituted by at least one unsubstituted $C_1$-$C_4$alkyl and/or substituted $C_1$-$C_4$alkyl, wherein the nitrogen atom can be quaternized.

$R_6$ is especially preferably phenyl unsubstituted or substituted by $C_1$-$C_4$alkyl, $C_1$-$C_4$alkoxy, halogen, phenyl or by hydroxyl; cyano; nitro; $-COOR_{12}$ or $-SO_3R_{12}$ wherein $R_{12}$ is in each case hydrogen, a cation, $C_1$-$C_4$alkyl or phenyl; $-SR_{13}$, $-SO_2R_{13}$ or $-OR_{13}$ wherein $R_{13}$ is in each case hydrogen, $C_1$-$C_4$alkyl or phenyl; $-N(CH_3)-NH_2$ or $-NH-NH_2$; amino; N-mono- or N,N-di-$C_1$-$C_4$alkylamino unsubstituted or substituted by hydroxy in the alkyl moiety, wherein the nitrogen atoms, especially the nitrogen atoms not bonded to one of the three pyridine rings A, B or C, may be quaternized; N-mono- or N,N-di-$C_1$-$C_4$alkyl-$N^{\oplus}R_{14}R_{15}R_{16}$ unsubstituted or substituted by hydroxy in the alkyl moiety, wherein $R_{14}$, $R_{15}$, and $R_{16}$ are each independently of the other(s) hydrogen, unsubstituted or hydroxyl-substituted $C_1$-$C_{12}$alkyl or phenyl unsubstituted or substituted as indicated above or $R_{14}$ and $R_{15}$ together with the nitrogen atom bonding them form a pyrrolidine, piperidine, piperazine, morpholine or azepane ring which is unsubstituted or substituted by at least one unsubstituted $C_1$-$C_4$alkyl and/or substituted $C_1$-$C_4$alkyl, wherein the nitrogen atom can be quaternized; N-mono- or N,N-di-$C_1$-$C_4$alkyl-$NR_{14}R_{15}$ unsubstituted or substituted by hydroxy in the alkyl moiety, wherein $R_{14}$ and $R_{15}$ can have one of the above meanings.

$R_6$ is very especially preferably $C_1$-$C_4$alkoxy; hydroxy; phenyl unsubstituted or substituted by $C_1$-$C_4$alkyl, $C_1$-$C_4$alkoxy, phenyl or hydroxy; hydrazine; amino; N-mono- or N,N-di-$C_1$-$C_4$alkylamino unsubstituted or substituted by hydroxy in the alkyl moiety, wherein the nitrogen atoms, especially the nitrogen atoms which are not bonded to one of the three pyridine rings A, B or C, may be quaternized; or a pyrrolidine, piperidine, morpholine or azepane ring unsubstituted or substituted by one or two unsubstituted $C_1$-$C_4$alkyl and/or substituted $C_1$-$C_4$alkyl, wherein the nitrogen atom can be quaternized.

A likewise very especially preferred radical $R_6$ is

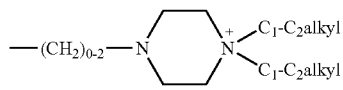

wherein the ring and the two alkyl groups may additionally be substituted.

Especially important as radicals $R_6$ are $C_1$-$C_4$alkoxy; hydroxy; hydrazine; amino; N-mono- or N,N-di-$C_1$-$C_4$alkylamino unsubstituted or substituted by hydroxy in the alkyl moiety, wherein the nitrogen atoms, especially the nitrogen atoms which are not bonded to one of the three pyridine rings A, B or C, may be quaternized; or a pyrrolidine, piperidine, piperazine, morpholine or azepane ring unsubstituted or substituted by at least one $C_1$-$C_4$alkyl, wherein the nitrogen atoms may be quaternized.

A further especially important example of $R_6$ is the radical

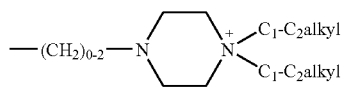

wherein the ring and the two alkyl groups may additionally be substituted.

Very especially important as radicals $R_6$ are $C_1$-$C_4$alkoxy; hydroxy; N-mono- or N,N-di-$C_1$-$C_4$alkylamino substituted by hydroxy in the alkyl moiety, wherein the nitrogen atoms, especially the nitrogen atoms which are not bonded to one of the three pyridine rings A, B or C, may be quaternized; or a pyrrolidine, piperidine, morpholine or azepane ring unsubstituted or substituted by at least one $C_1$-$C_4$alkyl, wherein the amino groups may be quaternized.

A further very especially important example of $R_6$ is the radical

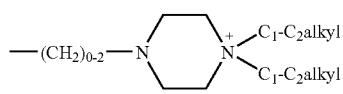

wherein the ring and the two alkyl groups may additionally be substituted.

As examples of the radical $R_6$, particular mention may be made of

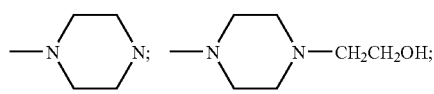

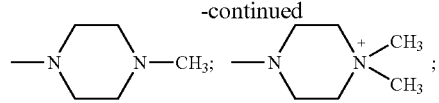

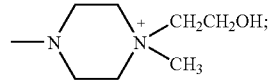

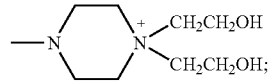

—NCH$_2$CH$_2\overset{+}{N}$(CH$_3$)$_3$;  —NCH$_2$CH$_2$N(CH$_3$)$_2$;
    |                                       |
   CH$_3$                                   CH$_3$ —NHCH$_2$CH$_2\overset{+}{N}$(CH$_3$)$_3$;  —NHCH$_2$CH$_2$N(CH$_3$)$_2$;
—N[CH$_2$CH$_2\overset{+}{N}$(CH$_3$)$_3$]$_2$;  —N[CH$_2$CH$_2$N(CH$_3$)$_2$]$_2$;
—N[CH$_2$CH$_2$CH$_2$N(CH$_3$)$_3$]$_2$;  and —N[CH$_2$CH$_2$CH$_2\overset{+}{N}$(CH$_3$)$_2$]$_2$.

—NHCH$_2$CH$_2$N(CH$_3$)$_3$;  —NHCH$_2$CH$_2$N(CH$_3$)$_2$;
—N[CH$_2$CH$_2$N$^+$(CH$_3$)$_3$]$_2$; —N[CH$_2$CH$_2$N(CH$_3$)$_2$]$_2$;
—N[CH$_2$CH$_2$CH$_2$N(CH$_3$)$_2$]$_2$ and —N[CH$_2$CH$_2$CH$_2$N(CH$_3$)$_3$]$_2$.

Hydroxyl is of particular interest here.

The preferred meanings given above for $R_6$ apply also to $R_1$, $R_2$, $R_3$, $R_4$, $R_5$, $R_7$, $R_8$, $R_9$, $R_{10}$ and $R_{11}$, but these radicals may additionally be hydrogen.

In accordance with one embodiment of the present invention, $R_1$, $R_2$, $R_3$, $R_4$, $R_5$, $R_7$, $R_8$, $R_9$, $R_{10}$ and $R_{11}$ are hydrogen and $R_6$ is a radical other than hydrogen having the definition and preferred meanings indicated above.

In accordance with a further embodiment of the present invention, $R_1$, $R_2$, $R_4$, $R_5$, $R_7$, $R_8$, $R_{10}$ and $R_{11}$ are hydrogen and $R_3$, $R_6$ and $R_9$ are radicals other than hydrogen having the definitions and preferred meanings indicated above for $R_6$.

In a likewise preferred use of metal complex compounds of the formula (1) as catalyst for oxidations, at least one of the substituents $R_1$—$R_{11}$, preferably $R_3$, $R_6$ and/or $R_9$, is one of the following radicals —($C_1$-$C_6$alkylene)-N$^\oplus$R$_{14}$R$_{15}$R$_{16}$; —N(R$_{13}$)—($C_1$-$C_6$alkylene)-N$^\oplus$R$_{14}$R$_{15}$R$_{16}$; —N[($C_1$-$C_6$alkylene)-N$^\oplus$R$_{14}$R$_{15}$R$_{16}$]$_2$; —N(R$_{13}$)—N$^\oplus$R$_{14}$R$_{15}$R$_{16}$, wherein $R_{13}$ is as defined above and $R_{14}$, $R_{15}$ and $R_{16}$ are preferably independently of the others hydrogen or substituted or unsubstituted $C_1$-$C_{18}$alkyl or aryl, or $R_{14}$ and $R_{15}$ together with the nitrogen atom bonding them form an substituted or substituted 5-, 6- or 7-membered ring which may contain further heteroatoms; or —NR$_{14}$R$_{15}$; —($C_1$-$C_6$alkylene)-NR$_{14}$R$_{15}$; —N(R$_{13}$)-($C_1$-$C_6$alkylene)-NR$_{14}$R$_{15}$; —N[($C_1$-$C_6$alkylene)-NR$_{14}$R$_{15}$]$_2$; —N(R$_{13}$)—N—R$_{14}$R$_{15}$ wherein R$_{13}$ and R$_{16}$ have the meanings indicated above and R$_{14}$ and R$_{15}$ together with the nitrogen atom bonding them form a 5-, 6- or 7-membered ring which is unsubstituted or substituted by at least one unsubstituted $C_1$-$C_4$alkyl and/or substituted $C_1$-$C_4$alkyl and may contain further heteroatoms, wherein at least one nitrogen atom which is not bonded to one of the pyridine rings A, B or C is quaternized.

In a likewise more preferred use of metal complex compounds of the formula (1) as catalyst for oxidation, at least one of the substituents $R_1$—$R_{11}$, preferably $R_3$, $R_6$ and/or $R_9$, is one of the following radicals —($C_1$-$C_4$alkylene)-N$^\oplus$R$_{14}$R$_{15}$R$_{16}$; —N(R$_{13}$)—($C_1$-$C_4$alkylene)-N$^\oplus$R$_{14}$R$_{15}$R$_{16}$; —N[($C_1$-$C_4$alkylene)-N$^\oplus$R$_{14}$R$_{15}$R$_{16}$]$_2$; —N(R$_{13}$)—

$N^{\oplus}R_{14}R_{15}R_{16}$, wherein $R_{13}$ is hydrogen, substituted or unsubstituted $C_1$-$C_{12}$alkyl or aryl and $R_{14}$, $R_{15}$ and $R_{16}$ are independently of the others hydrogen or substituted or unsubstituted $C_1$-$C_{12}$alkyl or aryl, or $R_{14}$ and $R_{15}$ together with the nitrogen atom bonding them form a 5-, 6- or 7-memered ring which is unsubstituted or substituted by at least one unsubstituted $C_1$-$C_4$alkyl and/or substituted $C_1$-$C_4$alkyl and may contain further heteroatoms; or —$NR_{14}R_{15}$; —($C_1$-$C_4$alkylene)-$NR_{14}R_{15}$; —$N(R_{13})$—($C_1$-$C_4$alkylene)-$NR_{14}R_{15}$; —$N[(C_1$-$C_4$alkylene)-$NR_{14}R_{15}]_2$; —$N(R_{13})$—$N$—$R_{14}R_{15}$, wherein $R_{13}$ and $R_{16}$ are independently of the other hydrogen, substituted or unsubstituted $C_1$-$C_{12}$alkyl or aryl and $R_{14}$ and $R_{16}$ together with the nitrogen atom bonding them form an unsubstituted or substituted 5-, 6- or 7-membered ring which may contain further heteroatoms, wherein at least one nitrogen atom which is not bonded to one of the pyridine rings A, B or C is quaternized.

In a likewise especially preferred use of metal complex compounds of the formula (1), at least one of the substituents $R_1$—$R_{11}$, preferably $R_3$, $R_6$ and/or $R_8$, is one of the following radicals —($C_1$-$C_4$alkylene)-$N^{\oplus}R_{14}R_{15}R_{16}$; —$N(R_{13})$—($C_1$-$C_6$alkylene)-$N^{\alpha}R_{14}R_{15}R_{16}$; —$N[(C_1$-$C_6$alkylene)-$N^{\oplus}R_{14}R_{15}R_{16}]_2$; —$N(R_{13})$—$N^{\oplus}R_{14}R_{15}R_{16}$, wherein $R_{13}$ is as defined above and $R_{14}$, $R_{15}$ and $R_{16}$ are independently of the others hydrogen or substituted or unsubstituted $C_1$-$C_{12}$alkyl or aryl, or $R_{14}$ and $R_{15}$ together with the nitrogen atom bonding them form a 5-, 6- or 7-membered ring which may be unsubstituted or substituted by at least one unsubstituted $C_1$-$C_4$alkyl and/or substituted $C_1$-$C_4$alkyl and may contain further heteroatoms; or —$NR_{14}R_{15}$; —($C_1$-$C_6$alkylene)-$NR_{14}R_{15}$; —$N(R_{13})$—($C_1$-$C_6$alkylene)-$NR_{14}R_{15}$; —$N[(C_1$-$C_6$alkylene)-$NR_{14}R_{15}]_2$; —$N(R_{13})$—$N$—$R_{14}R_{15}$ wherein $R_{13}$ and $R_{16}$ have the meanings indicated above and $R_{14}$ and $R_{15}$ together with the nitrogen atom bonding them form a substituted or unsubstituted 5-, 6- or 7-membered ring which may contain further heteroatoms, wherein the nitrogen atom which is not bound to one of the pyridine rings A, B or C is quaternized.

In a likewise important use of metal complex compounds of the formula (1), at least one of the substituents $R_1$—$R_{11}$, preferably $R_3$, $R_6$ and/or $R_9$, is a radical

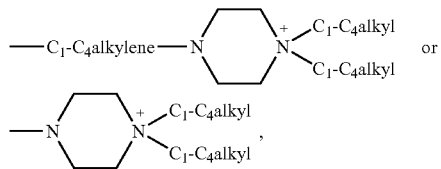

wherein the unbranched or branched alkylene group may be substituted and wherein the independently unbranched or branched alkyl groups may be substituted.

The piperazine ring may also be substituted.

In a likewise especially important use of metal complex compounds of the formula (1), at least one of the substituents $R_1$—$R_{11}$, preferably $R_3$, $R_6$ and/or $R_9$, is a radical

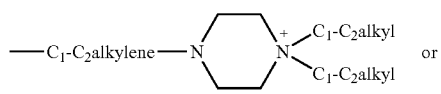

wherein the unbranched or branched alkylene groups may be substituted and wherein the alkyl groups may, independently of the other, be substituted.

The piperazine ring may also be substituted.

Preferred ligands L are those of the formula (3)

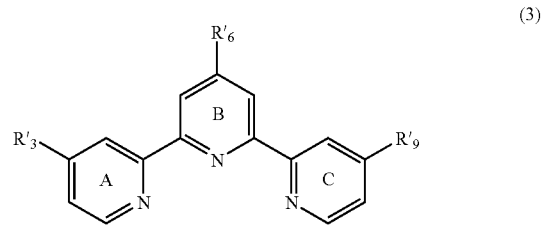

(3)

where $R'_3$, $R'_6$ and $R'_9$ have the definitions and preferred meanings indicated above for $R_6$, where $R'_3$ and $R'_9$ may additionally be hydrogen, likewise with the proviso that
(i) at least one of the substituents $R'_3$, $R'_6$ and/or $R'_9$ contains a quaternized nitrogen atom which is not directly bonded to one of the three pyridine rings A, B or C, and that
(ii) Y is neither I⁻ nor Cl⁻ in the case that Me is Mn(II), $R'_3$ and $R'_9$ are hydrogen and $R'_6$ is

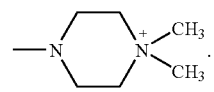

More preferred as ligands L are those of the formula (3)

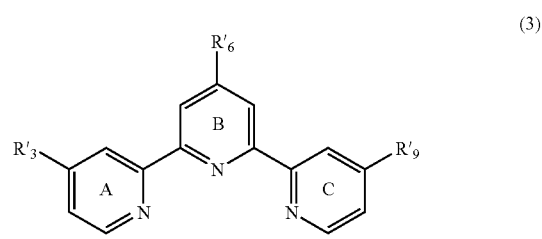

(3)

where $R'_3$, $R'_6$ and $R'_9$ have the definitions and preferred meanings indicated above for $R_6$, where $R'_3$ and $R'_9$ may additionally be hydrogen, with the proviso that
(i) at least one of the substituents $R'_3$, $R'_6$ and $R'_9$ is a radical —($C_1$-$C_6$alkylene)-$N^{\oplus}R_{14}R_{15}R_{16}$; —$N(R_{13})$—($C_1$-$C_6$alkylene)-$N^{\oplus}R_{14}R_{15}R_{16}$; —$N[(C_1$-$C_6$alkylene)-$N^{\oplus}R_{14}R_{15}R_{16}]_2$; —$N(R_{13})$—$N^{\oplus}R_{14}R_{15}R_{16}$, wherein $R_{13}$ is as above and $R_{14}$, $R_{15}$ and $R_{16}$ are independently of the others hydrogen or substituted or unsubstituted $C_1$-$C_8$alkyl or aryl, or $R_{14}$ and $R_{15}$ together with the nitrogen atom bonding them form a substituted or unsubstituted 5-, 6- or 7-membered ring which may contain further heteroatoms; or —NR$_{14}$R$_{15}$; —(C$_1$-C$_6$alkylene)-NR$_{14}$R$_{15}$; —N(R$_{13}$)—(C$_1$-C$_6$alkylene)-NR$_{14}$R$_{15}$; —N[(C$_1$-C$_6$alkylene)-NR$_{14}$R$_{15}$]$_2$; —N(R$_{13}$)—N—R$_{14}$R$_{15}$, wherein R$_{13}$ and R$_{16}$ have the meanings indicated above and R$_{14}$ and R$_{15}$ together with the nitrogen atom bonding them form a 5-, 6- or 7-membered ring which may be unsubstituted or substituted by at least one unsubstituted C$_1$-C$_4$alkyl and/or substituted C$_1$-C$_4$alkyl and may contain further heteroatoms, wherein at least one nitrogen atom which is not bonded to one of the pyridine rings A, B or C is quaternized, and that (ii) Y is neither I$^-$ nor Cl$^-$ in the case that Me is Mn(II), R'$_3$ and R'$_9$ are hydrogen and R'$_6$ is

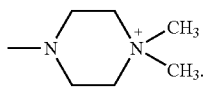

Even more preferred as ligands L are those of the formula (3)

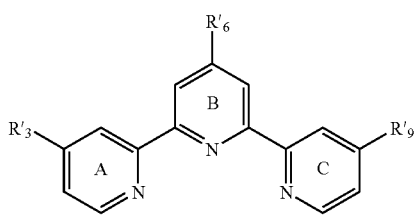

(3)

where R'$_3$, R'$_6$ and R'$_9$ have the definitions and preferred meanings indicated above for R$_6$, where R'$_3$ and R'$_9$ may additionally be hydrogen, with the proviso that (i) at least one of the substituents R'$_3$, R'$_6$ and R'$_9$ is one of the radicals

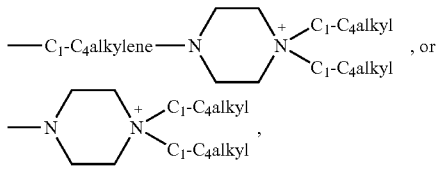

wherein the unbranched or branched alkylene group may be substituted, and wherein the independently unbranched or branched alkyl groups may be substituted and wherein the piperazine ring may be substituted, and that (ii) Y is neither I$^-$ nor Cl$^-$ in the case that Me is Mn(II), R'$_3$ and R'$_9$ are hydrogen and R'$_6$ is

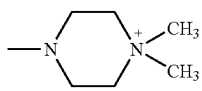

Especially preferred ligands L are those of the formula (3)

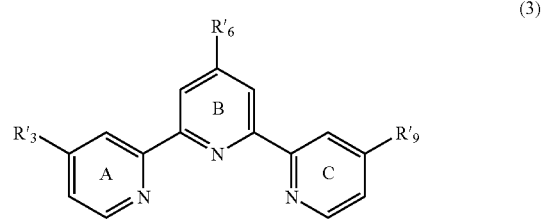

(3)

where R'$_3$, R'$_8$ and R'$_9$ have the definitions and preferred meanings indicated above for R$_6$, where R'$_3$ and R'$_9$ may additionally be hydrogen, with the proviso that (i) at least one of the substituents R'$_3$, R'$_8$ and R'$_9$ is one of the radicals

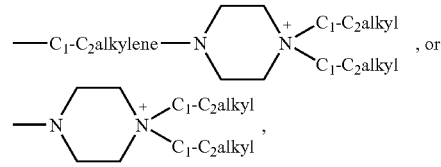

wherein the unbranched or branched alkylene group may be substituted, and wherein the independently unbranched or branched alkyl groups may be substituted and wherein the piperazine ring may be substituted, and that (ii) Y is neither I$^-$ nor Cl$^-$ in the case that Me is Mn(II), R'$_3$ and R'$_9$ are hydrogen and R'$_6$ is

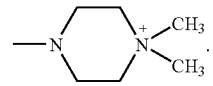

R'$_3$, R'$_6$ and R'$_9$ are preferably independently of the others phenyl unsubstituted or substituted by C$_1$-C$_4$alkyl, C$_1$-C$_4$alkoxy, halogen, phenyl or hydroxyl; cyano; nitro; —COOR$_{12}$ or —SO$_3$R$_{12}$, wherein R$_{12}$ is in each case hydrogen, a cation, C$_1$-C$_4$alkyl or phenyl; —SR$_{13}$, —SO$_2$R$_{13}$ or —OR$_{13}$, wherein R$_{13}$ is in each case hydrogen, C$_1$-C$_4$alkyl or phenyl; N(CH$_3$)—NH$_2$ or —NH—NH$_2$; amino; N-mono- or N,N-di-C$_1$-C$_4$alkylamino unsubstituted or substituted by hydroxy in the alkyl moiety, wherein the nitrogen atoms, especially the nitrogen atoms which are not bonded directly to one of the three pyridine rings A, B or C, may be quaternized; N-mono- or N,N-di-C$_1$-C$_4$alkyl-N$^\oplus$R$_{14}$R$_{15}$R$_{16}$ unsubstituted or substituted by hydroxy in the alkyl moiety, wherein R$_{14}$, R$_{15}$ and R$_{16}$ are each independently of the others hydrogen, unsubstituted or hydroxyl-substituted C$_1$-C$_{12}$alkyl or phenyl unsubstituted or substituted as indicated above or R$_{14}$ and R$_{15}$ together with the nitrogen atom bonding them form a pyrrolidine, piperidine, piperazine, morpholine or azepane ring unsubstituted or substituted by at least one C$_1$-C$_4$alkyl or by at least one unsubstituted C$_1$-C$_4$alkyl and/or substituted C$_1$-C$_4$alkyl, wherein the nitrogen atom may be quaternized; N-mono- or N,N-di-C$_1$-C$_4$alkyl-NR$_{14}$R$_{15}$ unsubstituted or substituted by hydroxy in the alkyl moiety, wherein R$_{14}$ and R$_{15}$ can have the meanings indicated above.

In particular, $R'_3$, $R'_6$ and $R'_9$ can each be a radical

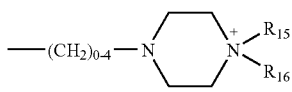

where $R_{15}$ and $R_{16}$ have the meanings indicated above and the ring may be substituted.

$R'_3$ and $R'_9$ can likewise be hydrogen.

Preference is given to compounds in which 1 quaternized nitrogen atom is present. Likewise preferred are compounds in which 2 or 3 quaternized nitrogen atoms are present. Particular preference is given to compounds in which all quaternized nitrogen atoms are not bonded directly to one of the pyridine rings A, B or C.

The metal complex compounds of the formula (1) can be obtained analogously to known processes. They are obtained in a manner known per se by reacting at least one ligand of the formula (2) in the desired molar ratio with a metal compound, especially a metal salt, such as the chloride, to form the corresponding metal complex. The reaction is carried out, for example, in a solvent, such as water or a lower alcohol, such as ethanol, at a temperature of, for example, from 10 to 60° C., especially at room temperature.

Ligands of the formula (2) that are substituted by hydroxyl can also be formulated as compounds having a pyridone structure in accordance with the following scheme:

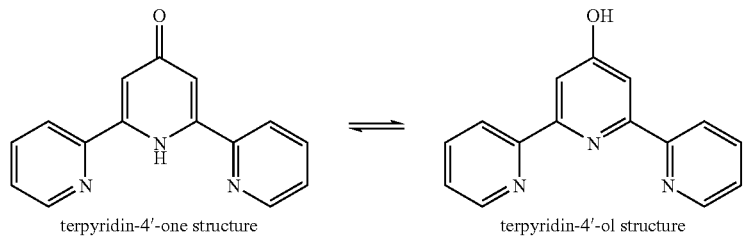

Generally, therefore, hydroxyl-substituted terpyridines are also to be understood as including those having a corresponding pyridone structure.

The ligands of the formula (2) can be prepared in a manner known per se. For this purpose, for example, a compound of the formula (4)

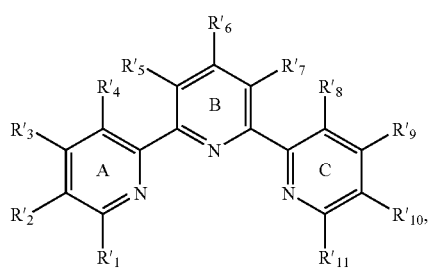

which contains no quaternized nitrogen atoms and in which $R'_1$—$R'_{11}$ have the definitions and preferred meanings indicated above for the substituents $R_1$—$R_{11}$, with the exception of quaternized nitrogen atoms and the proviso that at least one of the substituents $R'_1$—$R'_{11}$ contains halogen, $NO_2$ or $OR_{18}$, wherein $R_{18}$ is —$SO_2CH_3$ or tosylate, can be reacted with a corresponding stoichiometric amount of a compound of the formula (5)

$$HNR \qquad (5),$$

where R has one of the meanings of $R_1$—$R_{11}$, with the proviso that this contains a quaternizable nitrogen group which is not bonded directly to one of the three pyridine rings A, B or C. The stoichiometric amount of the compound (5) depends on the number of halogens, $NO_2$ or $OR_{18}$, wherein $R_{16}$ is as defined above, present in the compound of the formula (4). Preference is given to compounds of the formula (4) which have 1, 2 or 3 such radicals.

In a further step, the reaction product of the compound (4) and (5) is quaternized by means of known quaternizing agents, such as, in particular, methyl iodide or dimethyl sulfate, so that at least one quaternized nitrogen atom is present.

It has now been found that for the accelerated substitution of halide by amine on the terpyridine structure it is also possible to use catalytic amounts of non-transition metal salts, such as zinc(II) salts, which considerably simplifies the reaction procedure and working-up.

The present invention further relates to compounds of the formula (4)

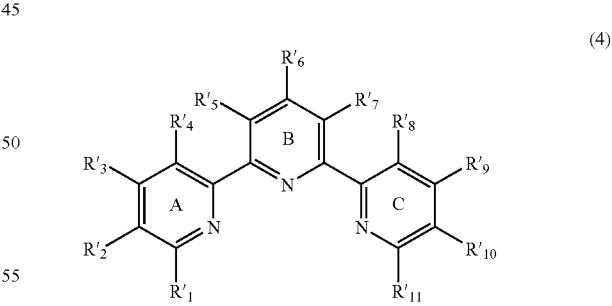

wherein
$R'_1$—$R'_{11}$ can have the definitions and preferred meanings indicated for the substituents
$R_1$—$R_{11}$, with the exception of quaternized nitrogen atoms and the proviso that
(i) at least one of the substituents $R'_1$—$R'_7$ is halogen, $NO_2$ or $OR_{18}$, wherein $R_{18}$ is —$SO_2CH_3$ or tosylate, and
(ii) the substituents $R'_8$—$R'_{11}$ are neither halogen, $NO_2$ nor $R_{18}$, wherein $R_{18}$ is as defined under (i).

The present invention further relates to compounds of the formula (4a) which are reaction products of the compounds of the formula (4) with the compounds of the formula (5)

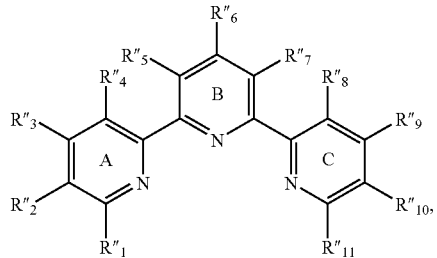

(4a)

wherein $R''_1$—$R''_{11}$ can have the definitions and preferred meanings indicated for the substituents $R_1$—$R_{11}$ with the exception of quaternized nitrogen atoms and the proviso that at least one of the substituents $R''_1$—$R''_7$ contains a quaternizable nitrogen group which is not bonded directly to one of the two pyridine rings A and/or B.

The compounds of the formula (4) can be prepared by methods known per se. These methods are described in K. T. Potts, D. Konwar, J. Org. Chem. 2000, 56, 4815-4816, E. C. Constable, M. D. Ward, J. Chem. Soc. Dalton Trans. 1990, 1405-1409, E. C. Constable, A. M. W. Cargill Thompson, New. J. Chem. 1992,16, 855-867, G. Lowe et al., J. Med. Chem., 1999, 42, 999-1006, E. C. Constable, P. Harveson, D. R. Smith, L. Whall, Polyhedron 1997,16,3615-3623, R. J. Sundberg, S. Jiang, Org. Prep. Proced. Int. 1997, 29,117-122, T. Sammakia, T. B. Hurley, J. Org. Chem. 2000, 65, 974-978 and J. Limburg et al., Science 1999, 283, 15241527.

The present invention further relates to the novel metal complex compounds of the formula (1a)

$$[L_nMe_mX_p]^zY_q \qquad (1a),$$

wherein Me is manganese, titanium, iron, cobalt, nickel or copper,

X is a coordinating or bridging radical, n and m are each independently of the other an integer having a value of from 1 to 8, p is an integer having a value from 0 to 32, z is the charge of the metal complex, Y is a counter-ion, q=z/(charge Y), and L is a ligand of the formula (2a)

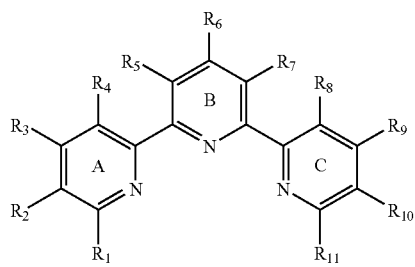

(2a)

wherein $R_6$ is substituted or unsubstituted $C_1$-$C_{18}$alkyl or aryl; cyano; halogen; nitro; —$COOR_{12}$ or —$SO_3R_{12}$, wherein $R_{12}$ is in each case hydrogen, a cation or substituted or unsubstituted $C_1$-$C_{18}$alkyl or aryl; —$SR_{13}$, —$SO_2R_{13}$ or -$OR_{13}$, wherein $R_{13}$ is in each case hydrogen or substituted or unsubstituted $C_1$-$C_{18}$alkyl or aryl; —$NR_{14}R_{15}$; —($C_1$-$C_6$alkylen)-$NR_{14}R_{15}$; —$N^{\oplus}R_{14}R_{15}R_{16}$; —($C_1$-$C_6$alkylene)-$N^{\oplus}R_{14}R_{15}R_{16}$; —$N(R_{13})$—($C_1$-$C_6$alkylene)-$NR_{14}R_{15}$; —$N[(C_1$-$C_6$alkylene)-$NR_{14}R_{15}]_2$; —$N(R_{13})$—($C_1$-$C_6$alkylene)-$N^{\oplus}R_{14}R_{15}R_{16}$; —$N[(C_1$-$C_6$alkylene)-$N^{\oplus}R_{14}R_{15}R_{16}]_2$; —$N(R_{13})$—N—$R_{14}R_{15}$ or —$N(R_{13})$—$N^{\oplus}R_{14}R_{15}R_{16}$, wherein $R_{13}$ is as defined above and $R_{14}$, $R_{15}$ and $R_{16}$ are each independently of the other(s) hydrogen or substituted or unsubstituted $C_1$-$C_{18}$alkyl or aryl, or $R_{14}$ and $R_{15}$ together with the nitrogen atom bonding them form a substituted or unsubstituted 5, 6- or 7-membered ring which may contain further heteroatoms, and $R_1$, $R_2$, $R_3$, $R_4$, $R_5$, $R_7$, $R_8$, $R_9$, $R_{10}$ and $R_{11}$ are independently of the others as defined above for $R_6$ or hydrogen or substituted or unsubstituted aryl, with the proviso that (i) at least one of the substituents $R_1$—$R_{11}$ contains a quaternized nitrogen atom which is not bonded directly to one of the three pyridine rings A, B or C, and that (ii) Y is neither I⁻ nor Cl⁻ in the case that Me is Mn, $R_1$—$R_5$ and $R_7$—$R_{11}$ are hydrogen and $R_6$ is

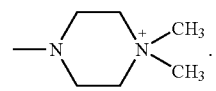

The definitions and preferred meanings indicated above for the compounds of the formula (1) also apply to the metal complex compounds of the formula (1a).

The ligand L of the metal complex compounds of the formula (1a) is especially a compound of the formula (3)

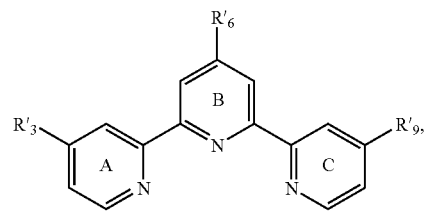

(3)

wherein $R'_6$ is $C_1$-$C_{12}$alkyl; phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthyl-amino, phenyl, phenoxy or by naphthoxy; cyano; halogen; nitro; —$COOR_{12}$ or —$SO_3R_{12}$ wherein $R_{12}$ is in each case hydrogen, a cation, $C_1$-$C_{12}$alkyl, or phenyl unsubstituted or substituted as indicated above; —$SR_{13}$, —$SO_2R_{13}$ or —$OR_{13}$ wherein $R_{13}$ is in each case hydrogen, $C_1$-$C_{12}$alkyl, or phenyl unsubstituted or substituted as indicated above; —$NR_{14}R_{15}$; —($C_1$-$C_6$alkylene)-$NR_{14}R_{15}$; —$N^{\oplus}R_{14}R_{15}R_{16}$; —($C_1$-$C_6$alkylene)-$N^{\oplus}R_{14}R_{15}R_{16}$; —$N(R_{13})$—($C_1$-$C_6$alkylene)-$NR_{14}R_{15}$; —$N[(C_1$-$C_6$alkylene)-$NR_{14}R_{15}]_2$; —$N(R_{13})$—($C_1$-$C_6$alkylene)-$N^{\oplus}R_{14}R_{15}R_{16}$; —$N[(C_1$-$C_6$alkylene)-$N^{\oplus}R_{14}R_{15}R_{16}]_2$; —$N(R_{13})$—N—$R_{14}R_{15}$ or —$N(R_{13})$—$N^{\oplus}R_{14}R_{15}R_{16}$, wherein $R_{13}$ can have one of the above meanings and $R_{14}$, $R_{15}$ and $R_{16}$ are each independently of the others hydrogen, unsubstituted or hydroxysubstituted $C_1$-$C_{12}$alkyl, or phenyl unsubstituted or substituted as indicated above, or $R_{14}$ and $R_{15}$ together with the nitrogen atom bonding them form a pyrrolidine, piperidine, piperazine, morpholine or azepane ring unsubstituted or substituted by at least one unsubstituted $C_1$-$C_4$alkyl and/or substituted $C_1$-$C_4$alkyl, wherein the nitrogen atom can be quaternized, and $R'_3$ and $R'_9$ are as defined above or are hydrogen, with the proviso that
(i) at least one of the substituents $R'_3$, $R'_6$ and $R'_9$ is a radical —($C_1$-$C_6$alkylene)-$N^\oplus R_{14}R_{15}R_{16}$, —$N(R_{13})$—($C_1$-$C_6$alkylene)-$N^\oplus R_{14}R_{15}R_{16}$, —$N[(C_1$-$C_6$alkylene)-$N^\oplus R_{14}R_{15}R_{16}]_2$, —$N(R_{13})$—$N^\oplus R_{14}R_{15}R_{16}$, wherein $R_{13}$ is as defined above and $R_{14}$, $R_{15}$ and $R_{16}$ are each independently of the others hydrogen or substituted or unsubstituted $C_1$-$C_{18}$alkyl or aryl, or $R_{14}$ and $R_{15}$ together with the nitrogen atom bonding them form a substituted or unsubstituted 5-, 6- or 7-membered ring which may contain further heteroatoms; or —$NR_{14}R_{15}$, —($C_1$-$C_6$alkylene)-$NR_{14}R_{15}$, —$N(R_{13})$—($C_1$-$C_6$alkylene)-$NR_{14}R_{15}$, —$N[(C_1$-$C_6$alkylene)-$NR_{14}R_{15}]_2$, —$N(R_{13})$—$N$—$R_{14}R_{15}$ wherein $R_{13}$ and $R_{16}$ have the meanings indicated above and $R_{14}$ and $R_{15}$ together with the nitrogen atom bonding them form a 5-, 6- or 7-membered ring which may be unsubstituted or substituted by at least one unsubstituted $C_1$-$C_4$alkyl and/or substituted $C_1$-$C_4$alkyl and may contain further heteroatoms, wherein at least one nitrogen atom which is not bonded to one of the pyridine rings A, B or C is quaternized, and that
(iii) Y is neither I⁻ nor Cl⁻ in the case that Me is Mn(II), $R'_3$ and $R'_9$ are hydrogen and $R'_6$ is

The definitions and preferred meanings indicated above for $R'_6$ and $R'_3$ and $R'_9$ likewise apply here.

The present invention relates also to the novel ligands of formula (2b)

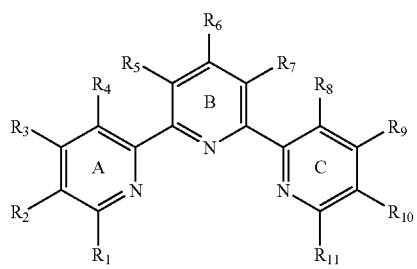

wherein $R_6$ is cyano; halogen; nitro; —$COOR_{12}$ or —$SO_3R_{12}$ wherein $R_{12}$ is in each case hydrogen, a cation or unsubstituted or substituted $C_1$-$C_{18}$alkyl or aryl; —$SR_{13}$, —$SO_2R_{13}$ or —$OR_{13}$ wherein $R_{13}$ is in each case hydrogen or unsubstituted or substituted $C_1$-$C_{18}$alkyl or aryl; —$NR_{14}R_{15}$, —$N^\oplus R_{14}R_{15}R_{16}$, —$N(R_{13})$—$(CH_2)_{1-6}NR_{14}R_{15}$, —$N(R_{13})$—$(CH_2)_{1-6}$—$N^\oplus R_{14}R_{15}R_{16}$, —$N(R_{13})$—$N$—$R_{14}R_{15}$ or —$N(R_{13})$—$N^\oplus R_{14}R_{15}R_{16}$, wherein $R_{13}$ can have one of the above meanings and $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form a pyrrolidine, piperidine, piperazine, morpholine or azepane ring unsubstituted or substituted by at least one unsubstituted $C_1$-$C_4$alkyl and/or substituted $C_1$-$C_4$alkyl, wherein the nitrogen atom may be quaternized; or a radical

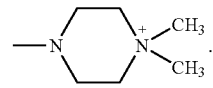

wherein $R_{15}$ and $R_{16}$ have the abovementioned meanings and the ring may be substituted, and $R_1$, $R_2$, $R_3$, $R_4$, $R_5$, $R_7$, $R_8$, $R_9$, $R_{10}$ and $R_{11}$ independently have the meanings indicated above for $R_6$ or are hydrogen or substituted or unsubstituted $C_1$-$C_{18}$alkyl or aryl, with the proviso that
(i) at least one of the substituents $R_1$—$R_{11}$ contains a quaternized nitrogen atom which is not bonded directly to one of the three pyridine rings A, B or C, and that
(ii) Y is neither I⁻ nor Cl⁻ in the case that $R_1$—$R_5$ and $R_7$—$R_{11}$ are hydrogen and $R_6$ is

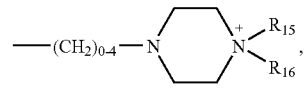

The definitions and preferred meanings indicated above for the ligands of the formula (2) also apply here.

Preference is given to ligands of formula (3)

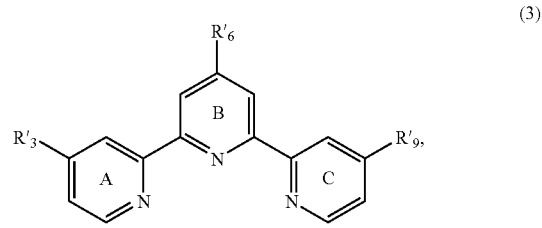

wherein $R'_6$ is cyano; halogen; nitro; —$COOR_{12}$ or —$SO_3R_{12}$, wherein $R_{12}$ is in each case hydrogen, a cation, $C_1$-$C_{12}$alkyl, or phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthyl-amino, where the amino groups may be quaternized, phenyl, phenoxy or naphthoxy; —$SR_{13}$, —$SO_2R_{13}$ or —$OR_{13}$, wherein $R_{13}$ is in each case hydrogen, $C_1$-$C_{12}$alkyl, or phenyl unsubstituted or substituted as indicated above; —$NR_{14}R_{15}$, —$N^\oplus R_{14}R_{15}R_{16}$, —$N(R_{13})$—$(CH_2)_{1-6}NR_{14}R_{15}$, —$N(R_{13})$—$(CH_2)_{1-6}$—$N^\oplus R_{14}R_{15}R_{16}$, —$N(R_{13})$—$N$—$R_{14}R_{15}$ or —$N(R_{13})$—$N^\oplus R_{14}R_{15}R_{16}$, wherein $R_{13}$ can have one of the above meanings, and $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form a pyrrolidine, piperidine, morpholine or azepane ring unsubstituted or substituted by at least one unsubstituted $C_1$-$C_4$alkyl and/or substituted $C_1$-$C_4$alkyl, wherein the nitrogen atom can be quaternized; or a radical

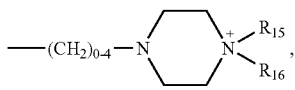

wherein $R_{15}$ and $R_{16}$ have the abovementioned meanings, preferably $C_1$-$C_4$alkyl, and the ring may be substituted, and $R'_3$ and $R'_9$ are as defined above or are hydrogen, $C_1$-$C_{12}$alkyl, or phenyl unsubstituted or substituted as indicated above. The definitions, provisos and preferred meanings indicated above for $R'_6$ and $R'_3$ and $R'_9$ for the ligands of the metal complex compounds of formula (3) likewise apply here.

In especially preferred ligands of the formula (3), $R'_3$ and $R'_6$ and $R'_9$ have the meanings given above and at least one of the substituents $R'_3$, $R'_8$ and $R'_9$ is a radical

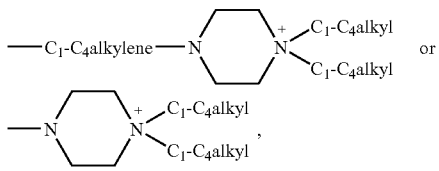

wherein the unbranched or branched alkylene group may be substituted and wherein the independently unbranched or branched alkyl groups may be substituted or wherein the piperazine ring may be substituted.

In very especially preferred ligands of the formula (3), $R'_3$, $R'_6$ and $R'_9$ have the meanings indicated above and at least one of the substituents $R'_3$, $R'_6$ and $R'_9$ is a radical

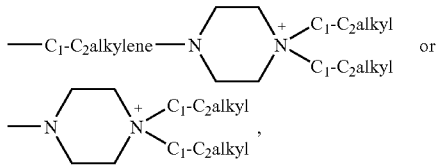

wherein the unbranched or branched alkylene group may be substituted and wherein the unbranched alkyl groups may be substituted independently of the other and wherein the piperazine ring may be substituted.

In even more especially preferred ligands of the formula (3), $R'_3$ and/or $R'_9$ are each a radical

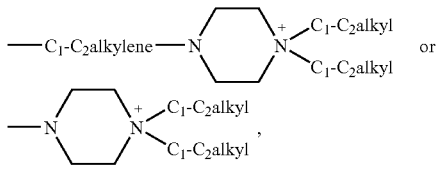

and $R'_6$ is OH.

The metal complex compounds of formula (1) are preferably used together with peroxy compounds. Examples that may be mentioned in that regard include the following uses:

a) the bleaching of spots or stains on textile material in the context of a washing process;
b) the prevention of redeposition of migrating dyes during the washing of textile material;
c) the cleaning of hard surfaces, especially wall tiles or floor tiles;
d) use in washing and cleaning solutions having an antibacterial action;
e) as pretreatment agents for bleaching textiles;
f) as catalysts in selective oxidation reactions in the context of organic synthesis,
g) as catalyst for the waste water treatment.

A further use relates to the use of the metal complex compounds of formula (1) as catalysts for reactions with peroxy compounds for bleaching in the context of paper-making. This relates especially to the delignification of cellulose respectively to the bleaching of pulp, which can be carried out in accordance with customary processes. Also of interest is the use of the metal complex compounds of formula (1) as catalysts for reactions with peroxy compounds for the bleaching of waste printed paper.

Preference is given to the bleaching of spots or stains on textile material, the prevention of the redeposition of migrating dyes in the context of a washing process, or the cleaning of hard surfaces, especially wall or floor tiles. The preferred metals are in this case manganese and/or iron.

It should be emphasised that the metal complex compounds do not cause any appreciable damage to fibres and dyeings, for example in the bleaching of textile material.

Processes for preventing the redeposition of migrating dyes in a washing liquor are usually carried out by adding to the washing liquor, which contains a peroxide-containing washing agent, one or more metal complex compounds of formula (1) in an amount of from 0.1 to 200 mg, preferably from 1 to 75 mg, especially from 3 to 50 mg, per litre of washing liquor.

Alternatively, it is possible to add a washing agent which already contains one or two metal complex compounds. It will be understood that in such an application, as well as in the other applications, the metal complex compounds of formula (1) can alternatively be formed in situ, the metal salt (e.g. manganese(II) salt, such as manganese(II) chloride, and/or iron(II) salt such as iron(II) chloride) and the ligand being added in the desired molar ratios.

The present invention relates also to a combined process for preventing the redeposition of migrating dyes and at the same time bleaching of spots or stains on textile material. For these purposes, use is made of mixtures of metal complexes of the formula (1), especially mixtures of manganese complexes of the formula (1) with iron complexes of the formula (1). Particular preference is given to mixtures of manganese complexes of the formula (1) with iron complexes of the formula (1'), which corresponds to the formula (1) but contains no quaternized nitrogen atoms. Processes for preventing the redeposition of migrating dyes in a washing liquor are usually carried out by adding to the washing liquor, which contains a peroxide-containing washing agent, the mixture of quaternized manganese complexes of the formula (1) and the non-quaternized iron complexes of the formula (1') in an amount of from 0.1 to 200 mg, preferably from 1 to 75 mg, especially from 3 to 50 mg, per litre of washing liquor. Alternatively, it is also possible to use an agent in which the appropriate metal complex mixture is already present. It will be understood that in this application, as well as in the other applications, the metal complex compounds of the formula (1) can alternatively be formed in situ, the metal salt (e.g. manganese(II)

salt, such as manganese(II) chloride, and/or iron(II) salt, such as iron(II) chloride) and the ligand being added in the desired molar ratios.

The present invention relates to mixtures of manganese complexes of the formula (1) with iron complexes of the formula (1'). The compounds of the formula (1') correspond to those of the formula (1) but there are no quaternized nitrogen atoms present.

The present invention relates also to a washing, cleaning, disinfecting or bleaching agent, containing I) 0-50%, preferably 0-30%, A) of an anionic surfactant and/or B) of a non-ionic surfactant,
II) 0-70%, preferably 0-50%, C) of a builder substance,
III) 1-99%, preferably 1-50%, D) of a peroxide or a peroxide-forming substance, and
IV) E) metal complex compounds of formula (1) in an amount which, in the liquor, gives a concentration of 0.5-50 mg/litre of liquor, preferably 1-30 mg/litre of liquor, when from 0.5 to 20 g/litre of the washing, cleaning, disinfecting and bleaching agent are added to the liquor.

The present invention relates also to a washing, cleaning, disinfecting or bleaching agent, containing I) 0-50%, preferably 0-30%, A) of an anionic surfactant and/or B) of a non-ionic surfactant,
II) 0-70%, preferably 0-50%, C) of a builder substance,
III) 0-10%, preferably 0-5% of phosphonates or aminoalkylene-poly(alkylenephosphonates),
IV) 1-99%, preferably 1-50%, D) of a peroxide or a peroxide-forming substance, and
V) E) metal complex compounds of formula (1) in an amount which, in the liquor, gives a concentration of 0.5-50 mgaitre of liquor, preferably 1-30 mgaitre of liquor, when from 0.5 to 20 gaitre of the washing, cleaning, disinfecting and bleaching agent are added to the liquor.

The above percentages are in each case percentages by weight, based on the total weight of the agent. The agents preferably contain from 0.005 to 2% of a metal complex compound of formula (1), especially from 0.01 to 1% and preferably from 0.05 to 1%.

When the agents according to the invention comprise a component A) and/or B), the amount thereof is preferably 1-50%, especially 1-30%.

When the agents according to the invention comprise phosphonates or aminoalkylene-poly(alkylenephosphonates), the amount thereof is preferably 1-3%, especially 0.1-3%.

When the agents according to the invention comprise a component C), the amount thereof is preferably 1-70%, especially 1-50%. Special preference is given to an amount of from 5 to 50% and especially an amount of from 10 to 50%.

Corresponding washing, cleaning, disinfecting or bleaching processes are usually carried out by using an aqueous liquor comprising a peroxide and from 0.1 to 200 mg of one or more compounds of formula (1) per litre of liquor. The liquor preferably contains from 1 to 30 mg of the compound of formula (1) per litre of liquor.

The agent according to the invention can be, for example, a peroxide-containing complete washing agent or a separate bleaching additive. A bleaching additive is used for removing coloured stains on textiles in a separate liquor before the clothes are washed with a bleach-free washing agent. A bleaching additive can also be used in a liquor together with a bleach-free washing agent.

Granules can be prepared, for example, by first preparing an initial powder by spray-drying an aqueous suspension containing all the components listed above except for components D) and E), and then adding the dry components D) and E) and mixing everything together. It is also possible to add component E) to an aqueous suspension containing components A), B) and C), then to carry out spray-drying and then to mix component D) with the dry mass.

It is also possible to start with an aqueous suspension that contains components A) and C), but none or only some of component B). The suspension is spray-dried, then component E) is mixed with component B) and added, and then component D) is mixed in in the dry state.

It is also possible to mix all the components together in the dry state.

The anionic surfactant A) can be, for example, a sulfate, sulfonate or carboxylate surfactant or a mixture thereof. Preferred sulfates are those having from 12 to 22 carbon atoms in the alkyl radical, optionally in combination with alkyl ethoxysulfates in which the alkyl radical has from 10 to 20 carbon atoms.

Preferred sulfonates are e.g. alkylbenzenesulfonates having from 9 to 15 carbon atoms in the alkyl radical. The cation in the case of anionic surfactants is preferably an alkali metal cation, especially sodium.

The anionic surfactant component may be, e.g., an alkylbenzenesulfonate, an alkylsulfate, an alkylethersulfate, an olefinsulfonate, an alkanesulfonate, a fatty acid salt, an alkyl or alkenyl ether carboxylate or an a-sulfofatty acid salt or an ester thereof. Preferred are alkylbenzenesulfonates having 10 to 20 carbon atoms in the alkyl group, alkylsulfates having 8 to 18 carbon atoms, alkylethersulfates having 8 to 18 carbon atoms, and fatty acid salts being derived from palm oil or tallow and having 8 to 18 carbon atoms. The average molar number of ethylene oxide added in the alkylethersulfate is preferably 1 to 20, preferably 1 to 10. The salts are preferably derived from an alkaline metal like sodium and potassium, especially sodium. Highly preferred carboxylates are alkali metal sarcosinates of formula R—$CO(R_1)CH_2COOM_t$ in which R is alkyl or alkenyl having 9-17 carbon atoms in the alkyl or alkenyl radical, $R_1$ is $C_1$-$C_4$ alkyl and $M_1$ is an alkali metal, especially sodium.

The nonionic surfactant component may be, e.g., primary and secondary alcohol ethoxylates, especially the $C_8$-$C_{20}$ aliphatic alcohols ethoxylated with an average of from 1 to 20 moles of ethylene oxide per mole of alcohol, and more especially the $C_{10}$-$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

The total amount of anionic surfactant and nonionic surfactant is preferably 5-50% by weight, preferably 540% by weight and more preferably 5-30% by weight. As to these surfactants it is preferred that the lower limit is 10% by weight. Preferred carboxylates are alkali metal sarcosinates of formula $R_{19}$—CO—N($R_{20}$)—$CH_2COOM'^1$ wherein $R_{19}$ is alkyl or alkenyl having from 8 to 18 carbon atoms in the alkyl or alkenyl radical, $R_{20}$ is $C_1$-$C_4$alkyl and $M'^1$ is an alkali metal.

The non-ionic surfactant B) can be, for example, a condensation product of from 3 to 8 mol of ethylene oxide with 1 mol of a primary alcohol having from 9 to 15 carbon atoms.

As builder substance C) there come into consideration, for example, alkali metal phosphates, especially tripolyphosphates, carbonates or hydrogen carbonates, especially their sodium salts, silicates, aluminosilicates, polycarboxylates, polycarboxylic acids, organic phosphonates, aminoalkylene-poly(alkylenephosphonates) or mixtures of those compounds.

Especially suitable silicates are sodium salts of crystalline layered silicates of the formula $NaHSi_tO_{2t+1} \cdot pH_2O$ or $Na_2Si_tO_{2t+1} \cdot pH_2O$ wherein t is a number from 1.9 to 4 and p is a number from 0 to 20.

Among the aluminosilicates, preference is given to those commercially available under the names zeolithe A, B, X and HS, and also to mixtures comprising two or more of those components. Zeolithe A is preferred.

Among the polycarboxylates, preference is given to polyhydroxycarboxylates, especially citrates, and acrylates and also copolymers thereof with maleic anhydride. Preferred poly-carboxylic acids are nitrilotriacetic acid, ethylenediaminetetraacetlc add and ethylene-diamine disuccinate either in racemic form or in the enantiomerically pure (S,S) form.

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid, hexamethylenediamin N,N,N',N' tetrakis methanphosphonic acid and diethylenetriaminepentamethylenephosphonic acid, as well as the salts therefrom.

Suitable peroxide components include, for example, the organic and inorganic peroxides (like sodium peroxides) known in the literature and available commercially that bleach textile materials at conventional washing temperatures, for example at from 5 to 95° C.

In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperacetates, diperoxypersebacates, diperoxyphthalates and/or diperoxydodecanedioates, especially their corresponding free acids, are of interest.

Especially preferred are mono-oder polyperoxide, especially organic peracids or their salts such as phthalimidoperoxycapronic acid, peroxybenzic acid, diperoxydodecandiacid, diperoxynonandiacid, diperoxydecandiacid, diperoxyphthalic add or their salts.

The amount of peroxide is preferably 0.5-30% by weight, preferably 1-20% by weight and more preferably 1-15% by weight. In case a peroxide is used, the lower limit is preferably 2% by weight, especially 5% by weight.

Preferably, however, inorganic peroxides are used, for example persulfates, perborates, percarbonates and/or persilicates. It will be understood that mixtures of inorganic and/or organic peroxides can also be used. The peroxides may be in a variety of crystalline forms and have different water contents, and they may also be used together with other inorganic or organic compounds in order to improve their storage stability.

The peroxides are added to the agent preferably by mixing the components, for example using a screw metering system and/or a fluidised bed mixer.

The agents may comprise, in addition to the combination according to the invention, one or more optical brighteners, for example from the class bis-triazinylamino-stilbenedisulfonic acid, bis-triazolyl-stilbenedisulfonic acid, bis-styryl-biphenyl or bis-benzofuranylbiphenyl, a bis-benzoxalyl derivative, bis-benzimidazolyl derivative or coumarin derivative or a pyrazoline derivative.

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; photobleaching agents; pigments; and/or shading agents. These constituents should, of course, be stable to any bleaching system employed. Such auxiliaries can be present in an amount of, for example, 0.1 to 20% by weight, preferably 0.5 to 10% by weight, especially 0.5 to 5% by weight, based on the total weight of the detergent.

Furthermore, the detergent can optionally contain enzymes. Enzymes can be added to detergents for stain removal. The enzymes usually improve the performance on stains that are either protein-or starch-based, such as those caused by blood, milk, grass or fruit juices. Preferred enzymes are cellulases, proteases, amylases and lipases. Preferred enzymes are cellulases and proteases, especially proteases. Cellulases are enzymes which act on cellulose and its derivatives and hydrolyze them into glucose, cellobiose, cellooligosaccharide. Cellulases remove dirt and have the effect of mitigating the roughness to the touch. Examples of enzymes to be used include, but are by no means limited to, the following:

proteases as given in US-B6,242,405, column 14, lines 21 to 32;
lipases as given in US-B-6,242,405, column 14, lines 33 to 46;
amylases as given in US-B-6,242,405, column 14, lines 47 to 56; and
cellulases as given in US-B-6,242,405, column 14, lines 57 to 64.

The enzymes can optionally be present in the detergent. When used, the enzymes are usually present in an amount of 0.01-5% by weight, preferably 0.05-5% and more preferably 0.1-4% by weight, based on the total weight of the detergent.

In addition to the bleach catalyst according to formula (1) it is also possible to use further transition metal salts or complexes known as bleach-activating active ingredients and/or conventional bleach activators, that is to say compounds that, under perhydrolysis conditions, yield unsubstituted or substituted perbenzo- and/or peroxo-carboxylic acids having from 1 to 10 carbon atoms, especially from 2 to 4 carbon atoms. Suitable bleach activators include the customary bleach activators, mentioned at the beginning, that carry O- and/or N-acyl groups having the indicated number of carbon atoms and/or unsubstituted or substituted benzoyl groups. Preference is given to polyacylated alkylenediamines, especially tetraacetylethylenediamine (TAED), acylated glycolurils, especially tetraacetylglycoluril (TAGU), N,N-diacetyl-N,N-dimethylurea (DDU), acylated triazine derivatives, especially 1,5diacetyl-2,4-dioxohexahydro-1,3,5-triazine (DADHT), compounds of formula (6):

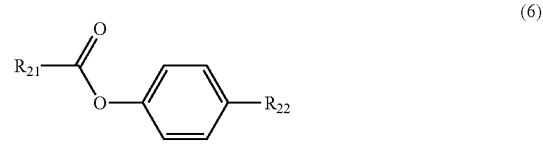

wherein $R_{21}$ is a sulfonate group, a carboxylic acid group or a carboxylate group, and wherein $R_{22}$ is linear or branched $(C_7-C_{15})$alkyl, especially activators known under the names SNOBS, SLOBS and DOBA, acylated polyhydric alcohols, especially triacetin, ethylene glycol diacetate and 2,5-diacetoxy-2,5-dhydrofuran, and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A44 43 177. Nitrile compounds that form perimine acids with peroxides also come into consideration as bleach activators.

Further preferred additives to the agents according to the invention are dye fixing agents and/or polymers which, during the washing of textiles, prevent staining caused by dyes in the washing liquor that have been released from the textiles under the washing conditions. Such polymers are preferably polyvinylpyrrolidones, polyvinylimidazole or polyvinylpyridine-N-oxides which may have been modified by the incorporation of anionic or cationic substituents, especially those having a molecular weight in the range of from 5000 to 60 000, more especially from 10 000 to 50 000. Such polymers are usually used in an amount of from 0.01 to 5%, preferably 0.05 to 5% by weight, especially 0.1 to 2% by weight, based on the total weight of the detergent. Preferred polymers are those given in WO-A-02102865 (see especially page 1, last paragraph and page 2, first paragraph).

The detergent compositions can take a variety of physical forms including powder, granular, tablet and liquid forms. Examples thereof are conventional powder heavy-duty detergents, compact and supercompact heavy-duty detergents and tablets, like heavy-duty detergent tablets. One important physical form is the so-called concentrated granular form adapted to be added to a washing machine.

Of importance are also the so-called compact (or supercompact) detergents. In the field of detergent manufacture, a trend has developed recently towards the production of compact detergents, which contain increased amounts of active substance. In order to minimize energy expenditure during the washing process, the compact detergents are required to operate efficiently at temperatures as low as 40° C., or even at room temperatures, e.g. at 25° C. Such detergents usually contain only low amounts of fillers or processing aids, like sodium sulfate or sodium chloride. The amount of such fillers is usually 0-10% by weight, preferably 05% by weight, especially 0-1% by weight, based on the total weight of the detergent. Such detergents usually have a bulk density of 650-1000 9g/l, preferably 700-1000 g/l and especially 750-1000 g/l.

The detergents can also be present in the form of tablets. Relevant characteristics of tablets are ease of dispensing and convenience in handling. Tablets are the most compact delivery of solid detergents and have a bulk density of, for example, 0.9 to 1.3 kg/litre. To enable fast disintegration laundry detergent tablets generally contain special disintegrants:
  Effervescents such as carbonate/hydrogencarbonate/citric acid;
  swelling agents like cellulose, carboxymethyl cellulose, cross-linked poly(N-vinylpyrrolidone);
  quickly dissolving materials such as Na (K) acetate, or Na (K) citrate;
  rapidly dissolving water-soluble rigid coating such as dicarboxy acids.

The tablets can also contain combinations of any of the above disintegrants.

The detergent may also be formulated as an aqueous liquid comprising 5-0, preferably 10-35% water or as a non-aqueous liquid detergent, containing not more than 5, preferably 0-1 wt. % of water. Non-aqueous liiquid detergent compositions can contain other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3propanediol, ethylene glycol, glycerine, and 1,2-propanediol) can also be used. The compositions may contain from 5% to 90%, typically 10% to 50% of such carriers. The detergents can also be present as the so-called "unit liquid dose" form.

The invention relates also to granules that comprise the catalysts according to the invention and are suitable for incorporation into a powder- or granule-form washing, cleaning or bleaching agent. Such granules preferably comprise:
a) from 1 to 99% by weight, preferably from 1 to 40% by weight, especially from 1 to 30% by weight, of a metal complex compound of formula (1), especially of formula (1a),
b) from 1 to 99% by weight, preferably from 10 to 99% by weight, especially from 20 to 80% by weight, of a binder,
c) from 0 to 20% by weight, especially from 1 to 20% by weight, of an encapsulating material,
d) from 0 to 20% by weight of a further additive and
e) from 0 to 20% by weight of water.

As binder (b) there come into consideration anionic dispersants, non-Ionic dispersants, polymers and waxes that are water-soluble, dispersible or emulsifiable in water.

The anionic dispersants used are, for example, commercially available water-soluble anionic dispersants for dyes, pigments etc.

The following products, especially, come into consideration: condensation products of aromatic sulfonic acids and formaldehyde, condensation products of aromatic sulfonic acids with unsubstituted or chlorinated diphenylene or diphenyl oxides and optionally formaldehyde, (mono-/di-)alkylnaphthalenesulfonates, sodium salts of polymerised organic sulfonic acids, sodium salts of polymerised alkylnaphthalenesulfonic acids, sodium salts of polymerised alkylbenzenesulfonic acids, alkylarylsulfonates, sodium salts of alkyl polyglycol ether sulfates, polyalkylated polynuclear arylsulfonates, methylene-linked condensation products of arylsulfonic acids and hydroxyarylsulfonic acids, sodium salts of dialkylsulfosuccinic acid, sodium salts of alkyl diglycol ether sulfates, sodium salts of polynaphthalenemethane-sulfonates, lignosulfonates or oxylignosulfonates or heterocyclic polysulfonic acids.

Especially suitable anionic dispersants are condensation products of naphthalenesulfonic acids with formaldehyde, sodium salts of polymerised organic sulfonic acids, (mono-di-)-alkylnaphthalenesulfonates, polyalkylated polynuclear arylsulfonates, sodium salts of polymerised alkylbenzenesulfonic acid, lignosulfonates, oxylignosulfonates and condensation products of naphthalenesulfonic acid with a polychloromethyidiphenyl.

Suitable non-ionic dispersants are especially compounds having a melting point of, preferably, at least 35° C. that are emulsifiable, dispersible or soluble, for example the following compounds:
1. fatty alcohols having from 8 to 22 carbon atoms, especially cetyl alcohol;
2. addition products of, preferably, from 2 to 80 mol of alkylene oxide, especially ethylene oxide, wherein some of the ethylene oxide units may have been replaced by substituted epoxides, such as styrene oxide and/or propylene oxide, with higher unsaturated or saturated monoalcohols, fatty acids, fatty amines or fatty amides having from 8 to 22 carbon atoms or with benzyl alcohols, phenyl phenols, benzyl phenols or alkyl phenols, the alkyl radicals of which have at least 4 carbon atoms;

3. alkylene oxide, especially propylene oxide, condensation products (block polymers);
4. ethylene oxide/propylene oxide adducts with diamines, especially ethylenedlamine;
5. reaction products of a fatty acid having from 8 to 22 carbon atoms and a primary or secondary amine having at least one hydroxy-lower alkyl or lower alkoxy-lower alkyl group, or alkylene oxide addition products of such hydroxyalkyl-group-containing reaction products;
6. sorbitan esters, preferably with long-chain ester groups, or ethoxylated sorbitan esters, such as polyoxyethylene sorbitan monolaurate having from 4 to 10 ethylene oxide units or polyoxyethylene sorbitan trioleate having from 4 to 20 ethylene oxide units;
7. addition products of propylene oxide with a tri- to hexa-hydric aliphatic alcohol having from 3 to 6 carbon atoms, e.g. glycerol or pentaerythritol; and
8. fatty alcohol polyglycol mixed ethers, especially addition products of from 3 to 30 mol of ethylene oxide and from 3 to 30 mol of propylene oxide with aliphatic monoalcohols having from 8 to 22 carbon atoms.

Especially suitable non-ionic dispersants are surfactants of formula

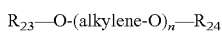

$$R_{23}\text{—O-(alkylene-O)}_n\text{—}R_{24} \quad (7),$$

wherein
$R_{23}$ is $C_8$-$C_{22}$alkyl or $C_8$-$C_{16}$alkenyl;
$R_{24}$ is hydrogen; $C_1$-$C_4$alkyl; a cycloaliphatic radical having at least 6 carbon atoms; or benzyl;
"alkylene" is an alkylene radical having from 2 to 4 carbon atoms and
n is a number from 1 to 60.

The substituents $R_{23}$ and $R_{24}$ in formula (7) are advantageously each the hydrocarbon radical of an unsaturated or, preferably, saturated aliphatic monoalcohol having from 8 to 22 carbon atoms. The hydrocarbon radical may be straight-chain or branched. R and R24 are preferably each independently of the other an alkyl radical having from 9 to 14 carbon atoms.

Aliphatic saturated monoalcohols that come into consideration include natural alcohols, e.g. lauryl alcohol, myristyl alcohol, cetyl alcohol or stearyl alcohol, and also synthetic alcohols, e.g. 2-ethylhexanol, 1,1,3,3-tetramethylbutanol, octan-2-ol, isononyl alcohol, trlmethy-hexanol, trimethyi-nonyl alcohol, decanol, $C_9$-$C_{11}$oxo-alcohol, tridecyl alcohol, isotridecyl alcohol and linear primary alcohols (Alfols) having from 8 to 22 carbon atoms. Some examples of such Alfols are Alfol (8-10), Alfol (9-11), Alfol (10-14), Alfol (12-13) and Alfol (16-18). ("Alfol" is a registered trade mark).

Unsaturated aliphatic monoalcohols are, for example, dodecenyl alcohol, hexadecenyl alcohol and oleyl alcohol.

The alcohol radicals may be present singly or in the form of mixtures of two or more components, e.g. mixtures of alkyl and/or alkenyl groups that are derived from soybean fatty acids, palm kernel fatty acids or tallow oils.

(Alkylene-O) chains are preferably divalent radicals of the formulae —(CH₂—CH₂—O)—,

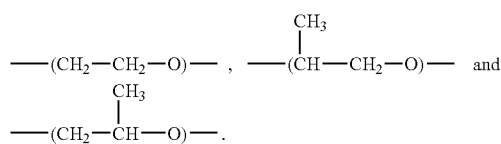

Examples of a cycloaliphatic radical are cycloheptyl, cyclooctyl and preferably cyclohexyl.

As non-ionic dispersants there come into consideration preferably surfactants of formula

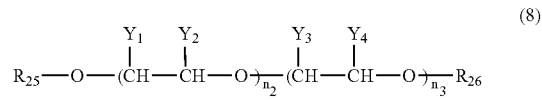

(8)

wherein
$R_{25}$ is $C_8$-$C_{22}$alkyl;
$R_{28}$ is hydrogen or $C_1$-$C_4$alkyl;
$Y_1, Y_2, Y_3$ and $Y_4$ are each independently of the others hydrogen, methyl or ethyl;
$n_2$ is a number from 0 to 8; and
$n_3$ is a number from 2 to 40.

Further important non-ionic dispersants correspond to formula

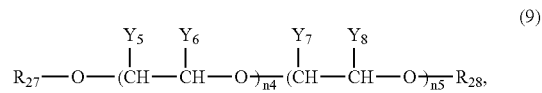

(9)

wherein
$R_{27}$ is $C_9$-$C_{14}$alkyl;
$R_{28}$ is $C_1$-$C_4$alkyl;
$Y_5, Y_6, Y_7$ and $Y_8$ are each independently of the others hydrogen, methyl or ethyl, one of the radicals $Y_5, Y_6$ and one of the radicals $Y_7, Y_8$ always being hydrogen; and $n_4$ and $n_5$ are each independently of the other an integer from 4 to 8.

The non-ionic dispersants of formulae (7) to (9) can be used in the form of mixtures. For example, as surfactant mixtures there come into consideration non-end-group-terminated fatty alcohol ethoxylates of formula (7), e.g. compounds of formula (7) wherein
$R_{23}$ is $C_8$-$C_{22}$alkyl,
$R_{24}$ is hydrogen and
the alkylene-O chain is the radical —(CH₂—CH₂—O)—
and also end-group-terminated fatty alcohol ethoxylates of formula (9).

Examples of non-ionic dispersants of formulae (7), (8) and (9) include reaction products of a $C_{10}$-$C_{13}$fatty alcohol, e.g. a $C_{13}$oxo-alcohol, with from 3 to 10 mol of ethylene oxide, propylene oxide and/or butylene oxide or the reaction product of one mol of a $C_{13}$fatty alcohol with 6 mol of ethylene oxide and 1 mol of butylene oxide, it being possible for the addition products each to be endgroup-terminated with $C_1$-$C_4$alkyl, preferably methyl or butyl.

Such dispersants can be used singly or in the form of mixtures of two or more dispersants.

Instead of, or in addition to, the anionic or non-ionic dispersant, the granules according to the invention may comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain α-olefins, copolymers of vinylpyrrolidone with vinylimidazole, poly(vinylpyrrolidoneldimethylaminoethyl methacrylates), copolymers of vinylpyrrolidoneldimethylaminopmpyl methacrylamides, copolymers of vinylpyrrolidoneldimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinyl-pyrrolidone/dimethylaminoethyl methacrylates, copolymers of styrene and acrylic acid, polycarboxylic acids, polyacrylamides, carboxymethylcellulose, hydroxymethylcellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxy-methylcellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolyrners of ethyl acrylate with methacrylate and methacrylic acid, and polymethacrylates.

Suitable water-emulsifiable or water-dispersible binders also include paraffin waxes.

Encapsulating materials (c) include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents.

The preparation of the granules according to the invention is carried out, for example, starting from:
a) a solution or suspension with a subsequent drying/shaping step or
b) a suspension of the active ingredient in a melt with subsequent shaping and solidification.
a) First of all the anionic or non-ionic dispersant and/or the polymer and, H appropriate, the further additives are dissolved in water and stirred, if desired with heating, until a homogeneous solution has been obtained. The catalyst according to the invention is then dissolved or suspended in the resulting aqueous solution. The solids content of the solution should preferably be at least 30% by weight, especially 40 to 50% by weight, based on the total weight of the solution. The viscosity of the solution is preferably less than 200 mPas.

The aqueous solution so prepared, comprising the catalyst according to the invention, is then subjected to a drying step in which all water, with the exception of a residual amount, is removed, solid particles (granules) being formed at the same time. Known methods are suitable for producing the granules from the aqueous solution. In principle, both continuous methods and discontinuous methods are suitable. Continuous methods are preferred, especially spray-drying and fluidised bed granulation processes.

Especially suitable are spray-drying processes in which the active ingredient solution is sprayed into a chamber with circulating hot air. The atomisation of the solution is effected e.g. using unitary or binary nozzles or is brought about by the spinning effect of a rapidly rotating disc. In order to increase the particle size, the spray-drying process may be combined with an additional agglomeration of the liquid particles with solid nuclei in a fluidised bed that forms an integral part of the chamber (so-called fluid spray). The fine particles (<100 μm) obtained by a conventional spray-drying process may, if necessary after being separated from the exhaust gas flow, be fed as nuclei, without further treatment, directly into the atomizing cone of the atomiser of the spray-dryer for the purpose of agglomeration with the liquid droplets of the active ingredient.

During the granulation step, the water can rapidly be removed from the solutions comprising the catalyst according to the invention, binder and further additives. It is expressly intended that agglomeration of the droplets forming in the atomising cone, or the agglomeration of droplets with solid particles, will take place.

If necessary, the granules formed in the spray-dryer are removed in a continuous process, for example by a sieving operation. The fines and the oversize particles are either recycled directly to the process (without being redissolved) or are dissolved in the liquid active ingredient formulation and subsequently granulated again.

A further preparation method according to a) is a process in which the polymer is mixed with water and then the catalyst is dissolved/suspended in the polymer solution, thus forming an aqueous phase, the catalyst according to the invention being homogeneously distributed in that phase. At the same time or subsequently, the aqueous phase is dispersed in a water-immiscible liquid in the presence of a dispersion stabiliser in order that a stable dispersion is formed. The water is then removed from the dispersion by distillation, forming substantially dry particles. In those particles, the catalyst is homogeneously distributed in the polymer matrix.

The granules according to the invention are wear-resistant, low in dust, pourable and readily meterable. They can be added directly to a formulation, such as a washing agent formulation, in the desired concentration of the catalyst according to the invention.

Where the coloured appearance of the granules in the washing agent is to be suppressed, this can be achieved, for example, by embedding the granules in a droplet of a whitish meltable substance ("water-soluble wax") or by adding a white pigment (e.g. $TiO_2$ to the granule formulation or, preferably, by encapsulating the granules in a melt consisting, for example, of a water-soluble wax, as described in EP-A-0 323 407, a white solid being added to the melt in order to reinforce the masking effect of the capsule.

b) The catalyst according to the invention is dried in a separate step prior to the melt-granulation and, if necessary, dryground in a mill so that all the solids particles are <50 μm in size. The drying is carried out in an apparatus customary for the purpose, for example in a paddle dryer, vacuum cabinet or freeze-dryer.

The finely particulate catalyst is suspended in the molten carrier material and homogenised. The desired granules are produced from the suspension in a shaping step with simultaneous solidification of the melt. The choice of a suitable melt-granulaflon process is made in accordance with the desired size of granules. In principle, any process which can be used to produce granules in a particle size of from 0.1 to 4 mm is suitable. Such processes are droplet processes (with solidification on a cooling belt or during free fall in cold air), melt-prilling (cooling medium gas/liquid), and flake formation with a subsequent comminution step, the granulation apparatus being operated continuously or discontinuously.

Where the coloured appearance of the granules prepared from a melt is to be suppressed in the washing agent, in addition to the catalyst it is also possible to suspend in the melt white or coloured pigments which, after solidification, impart the desired coloured appearance to the granules (e.g. titanium dioxide).

If desired, the granules can be covered or encapsulated in an encapsulating material. Methods suitable for such an encapsulation include the customary methods and also the encapsulation of the granules by a melt consisting e.g. of a water-soluble wax, as described, for example, in EP-A-0 323 407, coacervation, complex coacervation and surface polymerisation.

Encapsulating materials (c) include e.g. water-soluble, water-dispersible or water-emulsifiable polymers and waxes.

Further additives (d) include e.g. wetting agents, dust-removers, water-insoluble or water-soluble dyes or pigments, and also dissolution accelerators, optical brighteners and sequestering agents.

Surprisingly, the metal complex compounds of formula (1) also exhibit a markedly improved bleach-catalysing action on coloured stains which occur on wall or floor tiles.

The use of metal complex compounds of formula (1) as catalysts for reactions with peroxy compounds in cleaning solutions for hard surfaces, especially for wall or floor tiles, is therefore of special interest.

The metal complex compounds of formula (1) also have, together with peroxy compounds, excellent antibacterial action. The use of the metal complex compounds of formula (1) for killing bacteria or for protecting against bacterial attack is therefore likewise of interest.

The metal complex compounds of formula (1) are also outstandingly suitable for selective oxidation in the context of organic synthesis, especially the oxidation of organic molecules, e.g. of olefins to form epoxides. Such selective transformation reactions are required especially in process chemistry. The invention accordingly relates also to the use of the metal complex compounds of formula (1) in selective oxidation reactions in the context of organic synthesis.

The following Examples serve to illustrate the invention but do not limit the invention thereto. Parts and percentages relate to weight, unless otherwise indicated. Temperatures are in degrees Celsius, unless otherwise indicated.

EXAMPLE 1

Ethyl 4-chloropyridine-2-carboxylate

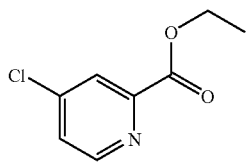

a) Step 1:

10.0 ml (0.130 mol) of N,N-dimethylformamide are added dropwise at 40° C. to 295 ml (4.06 mol) of thionyl chloride while stirring. 100 g (0.812 mol) of picolinic acid are subsequently added over the course of half an hour. The mixture is warmed carefully to 70° C. and stirred at this temperature for 24 hours, the gases formed being discharged via a wash bottle charged with sodium hydroxide solution. The mixture is evaporated, coevaporated another three times with 100 ml each time of toluene, diluted to 440 ml with the solvent and the solution is introduced into a mixture of 120 ml of absolute ethanol and 120 ml of toluene. The mixture concentrated to about half its volume, cooled to 4° C., filtered with suction and the solid is washed with toluene. Ethyl 4-chloropyridine-2-carboxylate hydrochloride is obtained as a beige, hygroscopic powder.

b) Step 2:

The hydrochloride obtained in step 1 is taken up in 300 ml of ethyl acetate and 200 ml of deionized water and rendered neutral with 4N sodium hydroxide solution. After phase separation, the aqueous phase is extracted twice more with 200 ml each time of ethyl acetate. The organic phases are combined, dried over sodium sulfate, filtered and concentrated. This gives ethyl 4chloropyridine-2-carboxylate as a brown oil which can be purified by distillation if required. $^1$H-NMR (360 MHz, CDCl$_3$): 8.56 (d, 1H, J=5.0 Hz); 8.03 (d, 1H, J=1.8 Hz); 7.39 (dd, 1H, J=5.4, 1.8 Hz); 4.39 (q, 2H, J=7.0 Hz); 1.35 (t, 3 H, J=7.0 Hz).

EXAMPLE 2

1-Pyridin-2-ylbutane-1,3-dione

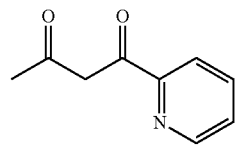

A solution of 8.71 g (150 mmol) of dry acetone in 100 ml of absolute tetrahydrofuran is added under argon to a solution of 20.42 g (300 mmol) of sodium ethoxide in 300 ml of absolute tetrahydrofuran. A solution of 22.68 g (150 mmol) of ethyl pyridine-2-carboxylate in 100 ml of absolute tetrahydrofuran is subsequently added dropwise over the course of 20 minutes. The mixture is stirred for 15 hours at room temperature and for 4 hours at the boiling point. The mixture is evaporated on a rotary evaporator, admixed with 150 ml of water and rendered neutral with glacial acetic acid. It is extracted twice with diethyl ether, the organic extracts are combined and dried (sodium sulfate), evaporated on a rotary evaporator, and 1-pyridin-2-ylbutane-1,3-dione is obtained as an orange oil. $^1$H-NMR (360 MHz, CDCl$_3$) for enol tautomer: 15.8-15.5 (br s, OH); 8.60-8.55 (dm, 1H); 8.20-7.95 (dm, 1H); 7.79-7.71 (tm, 1H); 7.35-7.29 (m, 1H); 6.74 (s, 1H); 2.15 (s, 3H). Keto tautomer: CH$_2$ group at 4.20 ppm (ratio of enol/keto form=87:13).

EXAMPLE 3

1-(4-Chloropyridin-2-yl)-5-pyridin-2-ylpentan-1,3,5-trione

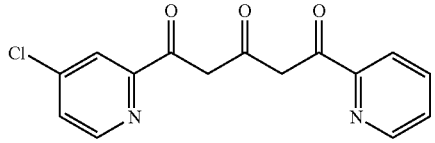

A mixture of 21.3 g (131 mmol) of 1-pyridin-2-ylbutane-1,3-dione and 36.3 g (196 mmol) of ethyl 4-chloropyridine-2-carboxylate in 100 ml of absolute tetrahydrofuran is added dropwise to 10.43 g (261 mmol, about 60% dispersion) of sodium hydride in 200 ml of absolute tetrahydrofuran at the boiling point over the course of two hours. The mixture is stirred for another two hours at 70° C., evaporated on a rotary evaporator, and 200 ml of water are subsequently added cautiously at 4° C. The mixture is rendered neutral with 5N hydrochloric acid, and 1-(4-chloropyridin-2-yl)-5-pyridin-2-ylpentane-1,3,5-trione is filtered off as a yellowish green solid The dried, sparingly soluble product is processed further without any particular purification steps.

EXAMPLE 4

4-Chloro1'H-[2,2';6',2"]terpyridin-4'-one

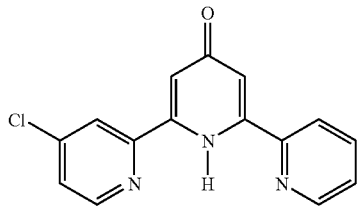

110 ml of 25 per cent strength ammonium hydroxide solution are added to 1-(4-chloropyridin-2-yl)-5-pyridin-2-yl-pentane-1,3,5-trione obtained as described above in 100 ml of isopropanol and the mixture is boiled under reflux for 4.5 hours. At room temperature, the pH is brought to 5 with 6N hydrochloric acid and the mixture is filtered. The residue is filtered through silica gel (eluent: chloroform/methanol/ammonium hydroxide solution 4:1:0.1) and evaporated. After recrystallization from acetone, 4-chloro-1'H-[2,2';6',2"]terpyridin-4'-one is obtained as a grey solid which is processed further without any particular purification steps. $^1$H-NMR (360 MHz, DMSO-de): 8.728.63 (m, 2H); 8.62-8.53 (m, 2H); 7.98 (ddd, 1H, J=7.7,7.7,1.8 Hz); 7.87 (d, 1H, J=2.2 Hz); 7.83 (d, 1H, J=2.2 Hz); 7.59 (dd, 1H, J=5.4,2.2 Hz); 7.43-7.51 (m, 1H); 2.07 (s, 1 H).

EXAMPLE 5

4-(4-Methylpiperazin-1-yl)-1'H-[2,2';6',2"]terpyridin-4'-one (Ligand L1)

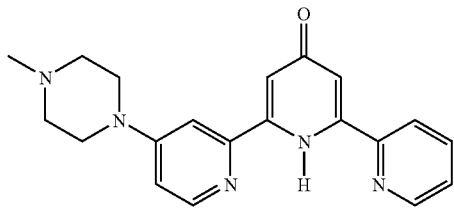

A mixture of 5.22 g (18.4 mmol) of 4-chloro-1'H-[2,2';6',2"]terpyridin-4'-one, 18.36 g (184 mmol, 20.4 ml) of 1-methylpiperazine and 125 mg (0.92 mmol, 0.05 equivalent) of zinc(II) chloride in 80 ml of 2-methyl-2-butanol is boiled under reflux for 30 hours. The mixture is evaporated to dryness on a rotary evaporator. 100 ml of water are added and the mixture is rendered neutral with concentrated hydrochloric acid. Extracting the mixture four times with chloroform and combining and drying (sodium sulfate) the organic extracts gives the crude product which is subsequently recrystallized from acetonitrile. 4-(4-Methyl-piperazin-1-yl)-1'H-[2,2';6',2"]terpyridin-4'-one is obtained as a white solid. $^1$H-NMR (360 MHz, CDCl$_3$): 8.69 (d, 1H, 4.5 Hz); 8.32 (d, 1H, J=5.9 Hz); 7.92-7.74 (m, 2H); 7.37-7.30 (m, 1H); 7.20 (d, 1H, J=2.3 Hz); 7.01 (s, 1H); 6.98 (s, 1H); 6.71-6.63 (m, 1H); 3.45-3.35 (tm, 4H); 2.58-2.48 (tm, 4H); 2.32 (s, 3H).

EXAMPLE 6

1,1-Dimethyl-4-(4'-oxo-1',4'-dihydro-[2,2';6',2"]terpyridin4yl)piperazin-1-Ium Methosulfate (Ligand L2)

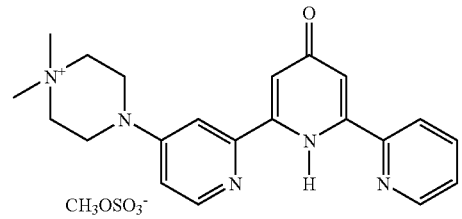

0.33 ml (3.5 mmol, 442 mg) of dimethyl sulfate is added dropwise to a suspension of 1.22 g (3.5 mmol) of 4-(4-methylpiperazin-1-yl)-1'H-[2,2';6',2"]terpyridin-4'-one in 60 ml of acetone. After 17 hours, the crude product is filtered off and washed (acetone or dichloromethane) and is subsequently recrystallized from methanol. 1,1-dimethyl-4-(4'-oxo-1',4'-dihydro-[2,2';6',2"]terpyridin-4-yl)piperazin-1-ium methosulfate is obtained as a white solid. $C_{22}H_{27}N_5O_5S*0.09\ H_2O$, 475.17; calculated C 55.61 H 5.77 N 14.74 S 6.75 H$_2$O 0.34; found C 55.56 H 5.85 N 14.63 S 6.75 H$_2$O 0.33. $^1$H-NMR (360 MHz, D$_2$O): 8.31 (d, 1H, J=4.1 Hz); 7.76 (dd, 1H, J=7.7); 7.64 (d, 1H, J=7.7 Hz); 7.58 (d, 1H, J=5.4 Hz); 7.22 (dd, 1H, J=7.2 5.0 Hz), 6.71 (s, 1H; 6.48 (dm, 1H); 6.46-6.39 (dm, 1H); 6.34 (dm, 1H); 3.67 (s, 3H); 3.48 (br s, 8 H); 3.19 (s, 6H).

EXAMPLE 7

Manganese(II) Complex with 1,1-dimethyl-4-(4'-oxo-1',4'-dihydro-[2,2';6',2"]terpyridin-4-yl)piperazin-1-ium Methosulfate A solution of 37.6 mg (0.19 mmol) of manganese(II) chloride tetrahydrate in 4 ml of methanol is added to a suspension of 1,1-dimethyl-4-(4'-oxo-1',4'-dihydro-[2,2';6',2"]terpyridin-4-yl)piperazin-1-ium methosulfate in 4 ml of methanol. The mixture is subsequently evaporated on a rotary evaporator (30° C., 20 mbar final pressure). The manganese complex of the formula $C_{22}H_{27}Cl_2MnN_5O_5S*0.38 H_2O$ (FW=606.24) is obtained as a yellow powder; calculated C 43.59 H 4.62 N 11.55 S 5.29 Cl 11.70 Mn 9.06 $H_2O$ 1.13; found C 43.54 H 4.50 N 11.73 S 5.07 Cl 11.69 Mn 9.06 $H_2O$ 1.14. (The manganse complex can alternatively be obtained without any loss of mass by a reaction in water followed by concentrating the solution or by lyophilisation.)

EXAMPLE 8

1,5-Bis(4-chloropyridin-2-yl)pentane-1,3,5-trione

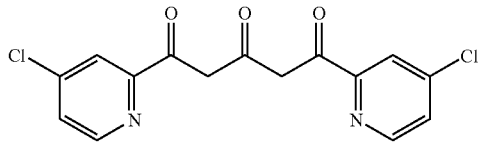

4 g (0.1 mol. about 60% dispersion) of sodium hydride in 100 ml of absolute tetrahydrofuran are placed in a reaction vessel under a nitrogen atmosphere. At <56° C., a solution of 18.5 g (0.1 mol) of ethyl 4-chloropyridine-2-carboxylate and 2.32 g (0.04 mol) of dried acetone in 75 ml of THF is added dropwise over the course of two hours. The red suspension is then carefully poured into 900 ml of water. It is rendered neutral with 6N HCl, tetrahydrofuran is distilled off on a rotary evaporator, and the yellow to beige 1,5-bis(4-chloropyridin-2-yl)pentane-1,3,5-trione formed is filtered off. The dried, sparingly soluble product is processed further without any particular purification steps. IR ($cm^{-1}$): 1619 (m); 1564 (s); 1546 (s); 1440 (m); 1374 (s); 1156 (m); 822 (w).

EXAMPLE 9

4,4"-Dichloro-1'H-[2,2';6',2"]terpyridin-4'-one

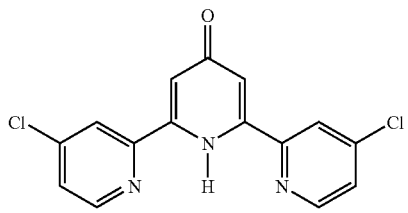

38.5 g (0.114 mol) of 1,5-bis(4-chloropyridin-2-yl)pentane-1,3,5-trione are suspended in 1.25 l of 2-propanol. A total of 230 ml of 25% (w/w) ammonia solution is added at 60° C.-70° C. over the course of five and a half hours. The mixture is cooled to 4° C. and the whitish 4,4"-dichloro-1'H-[2,2';6',2"]terpyridin-4'-one formed is filtered off. $^1$H-NMR (360 MHz, DMSO-$d_6$): 8.65 (d, 2H, J=5.4 Hz); 8.57 (d, 2H, J=2.2 Hz); 7.82 (s, 2H); 7.59 (dd, 2H, J=5.4,2.2 Hz).

EXAMPLE 10

4,4"-Bis(4-methylpiperazin-1-yl)-1'H-[2,2';6',2"]terpyridin-4'-one (Ligand L3)

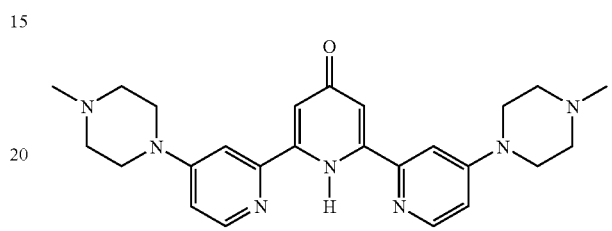

A mixture of 10.89 g (34.2 mmol) of 4,4"-dichloro-1'H-[2,2';6',2"]terpyridin-4'-one, 68.6 g (685 mmol, 76.1 ml) of 1-methylpiperazine and 233 mg (1.71 mmol, 0.05 equivalent) of zinc(II) chloride in 200 ml of 2-methyl-2-butanol is boiled under reflux for 24 hours. The mixture is evaporated to dryness on a rotary evaporator. The crude product is recrystallized from ethyl acetate/methanol 33:1 (v/v). It is taken up in 100 ml of water, adjusted to pH=8-9 with 4N sodium hydroxide solution, and light-beige 4,4"-bis(4methylpiperazin-1-yl)-1'H-[2,2';6',2"]terpyridin-4'-one is filtered off. $^1$H-NMR (360 MHz, CDCl$_3$): 8.32 (d, 2H, J=5.9 Hz); 7.18 (dm, 2H); 6.93 (s, 2H); 6.66 (dd, 2H; J=5.9,2.3 Hz); 3.41-3.32 (tm, 8H); 2.55-2.44 (tm, 8H); 2.29 (s, 6H).

EXAMPLE 10a 4,4"-bis-(4-butyl-piperazin-1-yl)-1'H-[2,2';6',2"]terpyridin-4'-on

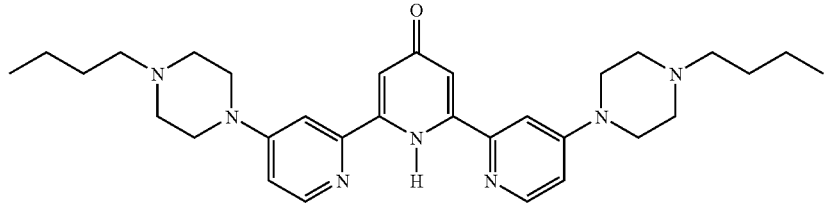

A mixture of 1.12 g (3.52 mmol) 4,4"-dichlor-1'H-[2,2';6',2"]terpyridin-4'-on, 10.0 g (70 mmol) 1-butyl-piperazine and 24 mg (0.18 mmol) Zn(II)-chloride in 20 ml 2-methyl-2butanol is refluxed for 18 hours. Afterwards, the solution is concentrated by a rotary evaporator. The raw product is recrystallized from a methanol/water mixture. The yellowish 4,4"-bis-(4-butyl-piperazin-1-yl)-1'H-[2,2';6',2"]terpyridin-4'-on is obtained. ¹H-NMR (360 MHz, CDCl₃): 8.31 (d, 2H, J=5.9 Hz); 7.18 (sm, 2H); 6.94 (s, 2H); 6.65 (dd, 2H, J=5.9, 1.8 Hz); 3.39-3.31 (tm, 8H); 2.55-2.47 (tm, 8H); 2.36-2,28 (tm, 4H); 1.5-1.38 (m, 4H); 1.36-1.22 (m, 4H); 0.87 (t, J=7.2 Hz, 6H).

EXAMPLE 10b

Double-Quaternisation of 4,4"-bis-(4butyl-piperazin-1-yl)-1'H-[2,2';6',2"]terpyridin-4'-on

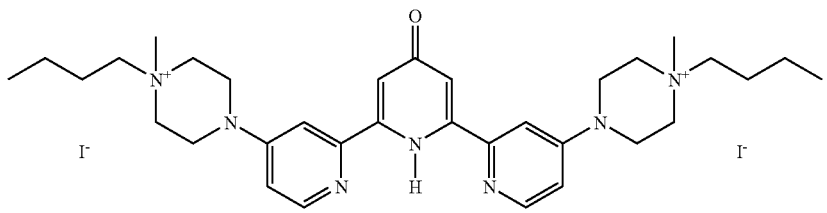

0.124 ml (1.99 mmol) of methyliodide are added dropwise to a suspension of 568 mg (0.994 mmol) 4,4"-bis-(4-methy-piperazin-1-yl)-1'H-[2,2';6',2"]terpyridin-4'-on in 18 ml acetonitril. The solution is stirred for 16 h at room temperature. The obtained whitish product ($C_{33}H_{49}I_2N_7O$) is filtered off and washed (with acetonitrile).

¹H-NMR (360 MHz, D₂O): 7.48 (d, 2H, J=6.8 Hz); 6.88 (sm, 2H); 6.75 (s, 2H); 6.69-6.61 (dm, 2H); 3.84 (m, 4H); 3.71 (m, 4H); 3.37 (m, 8H); 3.17 (m, 4H); 2.88 (s, 6H); 1.44 (m, 4H); 1.40 (m, 4H); 0.58 (t, 6H, 7.2 Hz).

EXAMPLE 10c 4,4"-bis-[4-(2-hydroxy-ethyl)-piperazin-1-yl)]-1'H-[2,2';6',2"]terpyridin-4'-on

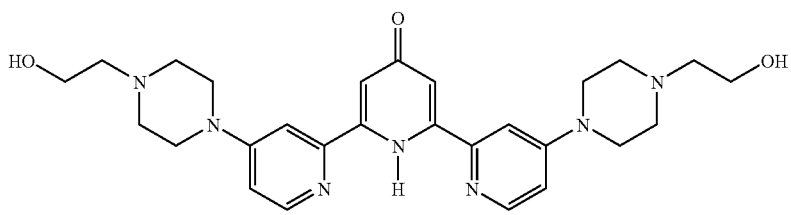

A mixture of 3.18 9 (10 mmol) 4,4"-dichlor-1'H-[2,2';6', 2"]terpyridin-4'-on, 5.21 g (40 mmol) 1-(2-hydroxyethyl)-piperazin, and 30 mg Zn(II)-chloride in 300 ml chlorobenzol is refluxed for 18 hours. Afterwards the solution is concentrated by a rotary evaporator. The raw product is recrystallized from 40 ml water respectively 30 ml methanol. The whitish 4,4"-Bis-[4-(2-hydroxy-ethyl)-piperazin-1-yl)]-1'H-[2,2';6',2"]terpyridin-4'-on is obtained.

¹H-NMR (360 MHz, DMSO-D6): 8.28 (dm, 2H); 8.08 (m, 2H); 7.75 (m, 2H); 6.92 (m, 2H); 3.64 (m, 4H); 3.44 (m, 8H); 2.57 (m, 8H); 2.52 (m, 4H).

EXAMPLE 10d

Double-Quaternisation of 4,4"-bis-[4-(2-hydroxy-ethyl)-piperazin-1-yl)]-1'H-[2,2';6',2"]terpyridin-4'-on

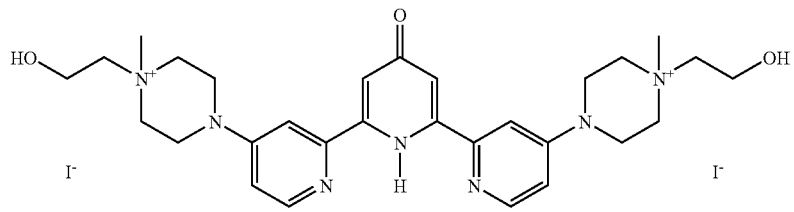

0.181 ml (3 mmol) of methyliodide are added dropwise to a suspension of 758 mg (ev. 1.5 mmol) 4,4"-bis-(4-methyl-piperazin-1-yl)-1'H-[2,2';6',2"]terpyridin-4'-on in 20 ml acetonitril. The solution is stirred for 16 h at room temperature. The obtained whitish product ($C_{29}H_{41}I_2N_7O_3$) is filtered off and washed (with acetonitrile).

$^1$H-NMR (360 MHz, $D_2O$+DCl): 8.37 (d, 2H, J=7.2 Hz); 8.17 (s, 2H); 7.99 (m, 2H); 7.39 (dm, 2H); 3.90-3.65 (m, H); 3.45-3.20 (m, 12H); 2.57 (m, 14H); 2.52 (m, 4H).

EXAMPLE 10e 4,4"-Bis-[(2-dimethylamino-ethyl)-methyl-amino]-1'H-[2,2';6',2"]terpyridin-4'-on

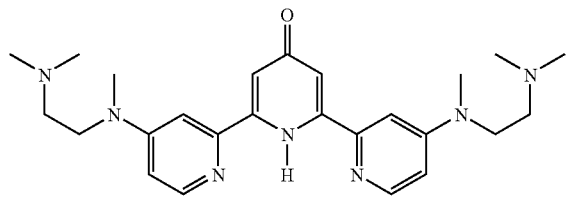

A mixture of 1.70 9 (5.34 mmol) 4,4"-Dichlor-1'H-[2,2';6',2"]terpyridin-4'-on, 13.8 ml (1.06 mmol) N,N,N'-Trimethylendiamin, and 36 mg Zn(II)-chloride in 300 ml chlorobenzol is refluxed for 2.5 days. Afterwards the solution is concentrated by a rotary evaporator. The raw product is recrystallized from 40 ml water respectively 30 ml methanol. The whitish 4,4"-bis-[(2-dimethylamino-ethyl)-methyl-amino]-1'H-[2,2';6',2"]terpyridin-4'-on is obtained. $^1$H-NMR (360 MHz, $D_2O$): 7.95 (d, 2H, 6.7 Hz); 6.98 (d, 2H, J=1.8 Hz); 6.90 (s, 2H); 6.71 (dd, 2H, J=6.7, 1.8 Hz); 3.72 (m, 4H); 3.14-3.0 (m, 10H); 2.70 (s, 12H).

EXAMPLE 10f

Double-Quaternisation of 4,4"-bis[(2-dimethy-lamino-ethyl)-methyl-amino]-1'H-[2,2';6',2"]terpyridin-4'-on

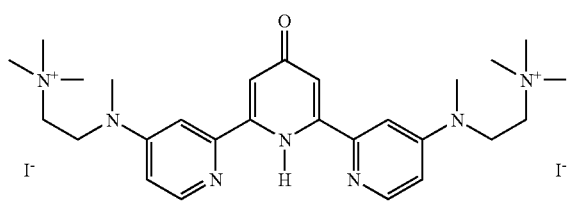

A solution of 0.036 ml (0.6 mmol) methyliodide in 4 ml acetonitrile are added dropwise to a suspension of 135 mg (0.3 mmol) 4,4"-Bis-[(2-dimethylamino-ethyl)-methyl-amino]-1'H-[2,2';6',2"]terpyridin-4'-on in 4 ml acetonitril. The solution is stirred for 16 h at room temperature. The obtained whitish product ($C_{27}H_{41}I_2N_7O$) is filtered off and washed (with acetonitrile).

$^1$H-NMR (360 MHz, $D_2O$): 8.14 (d, 2H, 6.3 Hz); 7.09 (d, 2H, J=2.2 Hz); 6.97 (s, 2H); 6.74 (dd, 2H, J=6.3,2.2 Hz); 3.95 (tm, 4H); 3.54 (tm, 4H); 3.20 (s,18H); 3.06 (s, 6H).

EXAMPLE 11

Double Quaternization of 4,4"-bis(4-methylpiperazin-1-yl)-1'H-[2,2';6',2"]terpyridin-4'-one with Methyl Iodide (Ligand L4)

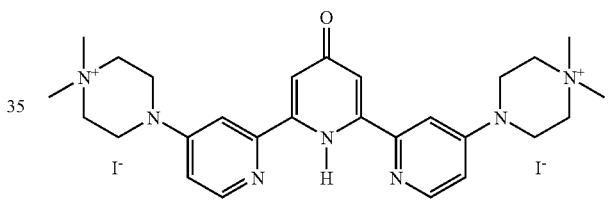

8.7 ml (19.9 g, 140 mmol) of methyl iodide are added dropwise to a suspension of 3.12 g (7 mmol) of 4,4"-bis(4methylpiperazin-1-yl)-1'H-[2,2';6',2"]terpyridin-4'-one in 150 ml acetonitrile. The mixture is stirred at room temperature for five hours, filtered and the resulting, doubly quaternized, whitish 4,4"-bis(4-methylpiperazin-1-yl)-1'H-[2,2';6',2"]terpyridin-4'-one ($C_{27}H_{37}I_2N_7O$) is washed (acetonitrile).

$^1$H-NMR (360 MHz, $D_2O$): 7.73 (d, 2H, J=5.9 Hz); 6.88 (s, 2H); 6.63-6.54 (dm, 2H); 6.45 (s, 2H); 3.69-3.43 (dm, 16H); 3.20 (s, 12H).

EXAMPLE 11a

Triple Methylation of 4,4"-bis(4-methylpiperazin-1-yl)-1'H-[2,2';6',2"]terpyridin-4'-one with Methyl Iodide (Ligand L4a)

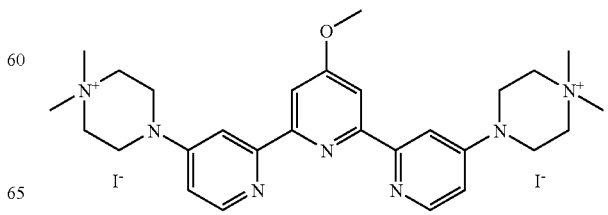

156 mg (0.35 mmol) of 4,4"-bis(4-methylpiperazin-1-yl)-1'H-[2,2';6',2]terpyridin-4'-one are added at 4° C. to a suspension of a total of about 30 mg of sodium hydride (about 0.75 mmol, 60 per cent strength in mineral oil) in 3 ml of absolute N,N-dimethylformamide. The mixture is stirred for another 20 minutes at this temperature, warmed to room temperature for one hour and cooled again. 66 µl (1.05 mmol) of methyl iodide are subsequently added dropwise, and the mixture is stirred for 20 minutes cold and for 30 minutes at room temperature. After the mixture has been cooled again and 2 ml of water have been added, white, triply methylated 4,4"-bis(4-methylpiperazin-1-yl)-1'H-[2,2';6',2"]terpyridin-4'-one of the formula $C_{28}H_{39}I_2N_7O$ is filtered off. $^{13}C$-NMR (40 MHz, DMSO-d$_6$): 167.2; 156.8; 155.6; 154.7; 149.8; 109.4; 106.4; 105.6; 59.9; 55.5; 50.4; 40.0.

EXAMPLE 12

Anion Exchange of L4 (Ligand L5)

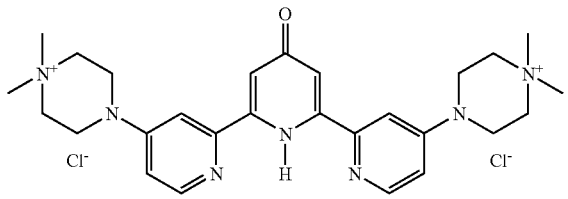

0.96 g (1.32 mmol) of 4,4"-bis(4-methylpiperazin-1-yl)-1'H-[2,2';6',2"]terpyridin-4'-one which has been double quaternized with methyl iodide is dissolved in 10 ml of dilute HCl (pH=6). The solution is eluted through an ion-exchange column (100 g DOWEX 1×8, 200-400 mesh, chloride form) and evaporated on a rotary evaporator. $C_{27}H_{37}Cl_2N_7O*1.8$ HCl*2 H$_2$O, calculated C 50.03 H 6.66 N 15.13 Cl 20.78, found C 50.47 H 6.67 N 14.90 Cl 20.4 (I content<0.3). $^1$H-NMR (400 MHz, D$_2$O): 8.17 (dm, 2H, J=7Hz); 7.59 (s, 2H); 7.46 (s, 2H); 7.15 (dm, 2H, J=7Hz); 4.14 (br s, 8H); 3.71 (br s, 8H); 3.30 (s, 12H).

EXAMPLE 13

Double Quaternization of 4,4"-bis(4-methylpiperazin-1-yl)-1'H-[2,2';6',2"]terpyridin-4'-one with dimethyl sulfate (Ligand L6)

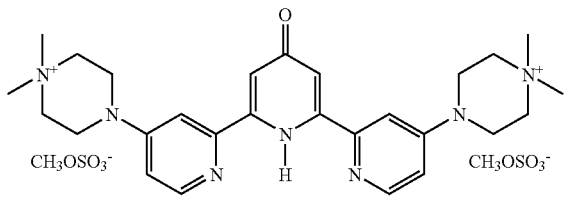

2.66 ml (27.92 mmol) of dimethyl sulfate are added dropwise to a suspension of 6.22 g (13.96 mmol) of 4,4"-bis(4-methylpiperazin-1-yl)-1'H-[2,2';6',2"]terpyridin-4'-one in 250 ml of acetone. After twenty hours, doubly quaternized, whitish 4,4"-bis(4-methylpiperazin-1-yl)-1'H-[2,2';6',2"]terpyridin-4'-one is filtered off and washed (acetone). $C_{29}H_{43}N_7O_9S_2*0.39$ H$_2$O, 704.86; calculated C 49.42 H 6.26 N 13.91 S 9.10 H$_2$O 1.00; found C 49.30 H 6.19 N 13.85 S 8.99 H$_2$O 1.00. $^1$H-NMR (360 MHz, D$_2$O): 8.08 (d, J=5.9 Hz, 2H); 7.18 (dm, 2H); 6.79 (dd, J=5.9,2.3 Hz); 6.74 (s, 2H); 3.77-3.68 (m, 8H); 3.65 (s, 6 H); 3.59-3.50 (m, 8H).

EXAMPLE 14

Manganese(II) Complex with Doubly Quaternized 4,4"-bis(4-methylpiperazin-1-yl)-1'H-[2,2';6',2"]terpyridin-4'-one A solution of 119 mg (0.6 mmol) of manganese(II) chloride tetrahydrate in 11 ml of methanol is added to a suspension of 419 mg (0.6 mmol) of the ligand $C_{29}H_{43}N_7O_9S_2$. The mixture is subsequently evaporated on a rotary evaporator (30° C., 20 mbar final pressure). The manganese complex of the formula $C_{29}H_{43}Cl_2MnN_7O_9S_2*2.22$ H$_2$O (FW 863.67) is obtained as a yellow powder; calculated C 40.33 H 5.54 N 11.35 S 7.43 Cl 8.21 Mn 6.36 H$_2$O 4.63; found C 41.10 H 5.35 N 11.77 S 7.18 Cl 8.36 Mn 5.91 H$_2$O 4.64.

APPLICATION EXAMPLES

Application Example 1

Bleaching Action in Washing Agents 7.5 g of white cotton fabric and 2.5 g of tea-stained cotton fabric are treated in 80 ml of washing liquor. The liquor contains a standard washing agent (IEC 60456 A*) in a concentration of 7.5 g/l. The hydrogen peroxide concentration is 8.6 mmol/l. The catalyst concentration (1:1 complex of manganese(II) chloride tetrahydrate with the ligand in question, prepared in methanolic or aqueous solution) is 20 µmol/l. The washing process is carried out in a steel beaker in a UNITEST apparatus for 30 minutes at 40° C. For evaluating the bleaching results, the increase in the lightness DY (difference in lightness according to CIE) of the stains brought about by the treatment is determined spectrophotometrically in comparison with values obtained without the addition of catalyst The Mn complex of the formula (10) listed in Table 1 below for comparative purposes is the compound of the formula

TABLE 1

(10)

| Mn complex with ligand | DY increase |
|---|---|
| L1 (Example 5) | 5.9 |
| L2 (Example 6) | 8.6 |
| L3 (Example 10) | 5.6 |
| L4 (Example 11) | 9.7 |
| L5 (Example 12) | 10.0 |
| L6 (Example 13) | 10.1 |
| Terpyridine (10) | 1.4 |

As can be seen from Table 1 above, the ligands according to the invention having a quaternized nitrogen function have a far better bleaching action thant the corresponding parent compounds. All complexes are distinctly superior to the terpyridine reference system.

Application Example 2

Catalytic Bleaching of Cellulose 20 g of cellulose [tmP-CT CSF129, Ref. No. P-178635 (ISO 57.4)] are steeped in a litre of water for 65 hours and then stirred in a mixer for 2 minutes to give a paste-like pulp. A bleaching bath containing 50 g of the pulp so prepared in 180 ml of water, 100 μM of Dequest 2041 (sequestering agent), 8.6 mM of hydrogen peroxide and 5 μM of catalyst from Example 14 is maintained at 40° C. for 30 minutes. At the same time 1N sodium hydroxide solution is metered-in in such a manner that a pH of 10.0 is maintained. Filtration and air-drying are then carried out. A sample that has been compressed to form a circular sheet of 10 cm diameter is then tested for the lightness Y obtained (according to CIE, reflectance spectroscopy). The results are compiled in the following Table 2.

TABLE 2

| Test sample | Lightness Y |
| --- | --- |
| untreated | 61.9 |
| catalytically bleached | 62.9 |

Application Example 2a

Delignification 5 g (dry weight) of Softwood cellulose having a kappa number of 26.4 and 71 ml of carbonate buffer (0.4% sodium hydrogencarbonate und 0.5% sodiumcarbonate) are put in to a plastic bag. 13.3 ml of a 30% H2O2 solution and 13.6 ppm of the catalyst of Example 14 are added. The obtained pulp is kneaded intensively and put into a water bath (40° C.) for 90 minutes. Afterwards the pulp is filtered and wash with hot water (60° C.). Afterwards, the kappa number is determined according to standardized test TAPPI T236 om-99 (TAPPI=Technical Association for the Pulp and Paper Industry). The determined kappa number is 19.3. The obtained kappa number in a comparison Example with the same condition but without the catalyst is 21.4.

The addition of the catalyst leads to a reduction of the kappa number.

Application Example 3

Action as Catalyst for DTI (Dye Transfer Inhibition

In accordance with this application, the redeposition of migrating dyes in washing liquors, especially, should be prevented.

7.5 g of white cotton fabric are treated in 80 ml of washing liquor. The liquor contains a standard washing agent (IEC 60456 A*) in a concentration of 7.5 g/l, 8.6 mmol/l of hydrogen peroxide and a solution of the test dye Reactive Blue 238. The catalyst solution is prepared beforehand in methanol by mixing an aqueous solution of equimolar amounts of iron(III) chloride and ligand L6 from Example 13. This is used to set a catalyst concentration of 50 μmol/l in the liquor. The washing process is carried out in a steel beaker in a LINITEST apparatus for 30 minutes at 40° C. For testing the activity of the catalysts, the DTI activity is determined. The DTI Lye Transfer Inhibition) activity a is defined as the following percentage.

$$a = ([Y(E) - Y(A)]/[Y(W) - Y(A)]) * 100$$

where Y(W), Y(A) and Y(E) are the CIE lightness values of the white material, of the material treated without the addition of catalyst and of the material treated with the addition of catalyst, in that order. a=100% corresponds to a perfect catalyst which totally prevents the staining of the white material.

The reflection spectra of the samples were measured using a SPECTRAFLASH 2000 and converted into lightness values (D65/10) in accordance with a standard CIE procedure. According to the test procedure described above, a value a=71% results.

Application Example 4

The use of the catalysts according to the invention causes hardly any additional fading of the dyes in dyed cotton laundry. When used as described above in Application Example 4, after treatment of coloured fabric five times, virtually no losses of dye are recorded compared with the catalyst-free system. The values given in the following Table 3 are relative percentage dye losses, determined on the basis of Kubelka-Munk values at the respective absorption maximum.

TABLE 3

| | Dye loss (%) in system | |
| --- | --- | --- |
| Cotton dyeing with dye | with MnCl$_2$-L4 (50 μM) | without catalyst |
| V Br 1 | 1 | 2 |
| V Bl 4 | 7 | 4 |
| R Br 17 | 13 | 15 |
| D Bl 85 | 19 | 14 |

Application Example 5

Catalytic Action for the Epoxidation of Olefins 35 mg (0.05 mmol) of ligand L6 (Example 13), 10 mg (0.04 mmol) of manganese(II) acetate tetrahydrate and 0.32 mmol of sodium ascorbate are added to a solution of 1.09 ml (10 mmol) of ethyl acrylate in 0.5 ml of acetonitrile. The mixture is cooled in an ice bath and a 30% strength hydrogen peroxide solution (2.27 g, 20 mmol) is added dropwise thereto in the course of 20 minutes. The mixture is then left for 16 hours at room temperature, then diluted with diethyl ether and the phases are separated. The organic extract is dried over sodium sulfate, filtered and concentrated. The catalytic turnover number for the epoxide formed, ethyl oxirane-2-carboxyate, is determined by comparing the intensity of the epoxide methine proton at 3.38-3.42 ppm with an olefin signal of the remaining starting material at 5.95 ppm as reference and is 39±5. Ethyl oxirane-2-carboxylate, epoxide signals $^1$H-NMR (360 MHz, CDCl$_3$): 2.68-2.89 (m, 2H, CH$_2$); 3.38-3.42 (m, 1H, CH). Without the addition of ligand, epoxide cannot be detected.

(see in this connection also Berkessel, A. et al., Tetrahedron Lett. 1999, 40, 7965-7968).

What is claimed is:

1. A metal complex compound of formula (1a)

$$[L_nMe_mX_p]^zY_q \quad (1a),$$

wherein Me is manganese which is present in oxidation state II, III, IV or V, or iron which is present in oxidation state II, III or IV, X is a coordinating or bridging radical, n and m are each independently of the other an integer having a value of from 1 to 8, p is an integer having a value from 0 to 32, z is the charge of the metal complex, Y is a counter-ion, q=z/(charge Y), and ligand L is a compound of formula (3)

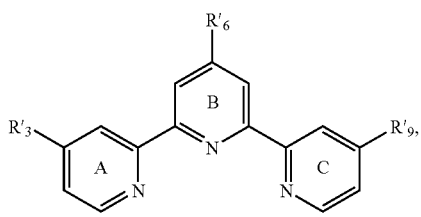

wherein $R'_6$ is cyano; halogen; nitro; —$COOR_{12}$ or —$SO_3R_{12}$; —$SR_{13}$, —$SO_2R_{13}$ or —$OR_{13}$; —$N(R_{13})$—$(CH_2)_{1-6}$$NR_{14}R_{15}$; —$N(R_{13})$—$(CH_2)_{1-6}$—$N^{\oplus}R_{14}R_{15}R_{16}$; —$N(R_{13})$—$N$—$R_{14}R_{15}$ or —$N(R_{13})$—$N^{\oplus}R_{14}R_{15}R_{16}$, wherein $R_{12}$ is in each case hydrogen, a cation, $C_1$-$C_{12}$alkyl, or phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, where the amino groups may be quaternized, phenyl, phenoxy or by naphthoxy;

$R_{13}$ is in each case hydrogen, $C_1$-$C_{12}$alkyl, or phenyl unsubstituted or substituted as indicated above;

and $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form a pyrrolidine, piperidine, morpholine or azepane ring which is unsubstituted or substituted by at least one unsubstituted $C_1$-$C_4$alkyl and/or substituted $C_1$-$C_4$alkyl;

or a radical

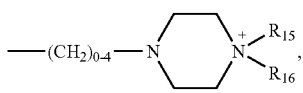

wherein $R_{15}$ and $R_{16}$ are as defined above; and $R'_3$ and $R'_9$ are as defined above for $R'_6$ or are hydrogen, $C_1$-$C_{12}$alkyl, or phenyl unsubstituted or substituted as indicated above, with the proviso that (i) at least one of the substituents $R_3'$, $R_6'$ and $R_9'$ contains a quaternized nitrogen atom which is not directly bonded to one of the three pyridine rings A, B or C

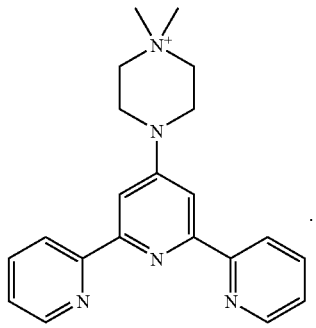

2. A method of catalyzing an oxidation reaction which comprises oxidizing a substrate in the presence of a catalytically effective amount of a metal complex compound of formula (1a)

$$[L_nMe_mX_p]^zY_q \quad (1a),$$

wherein Me is manganese which is present in oxidation state II, III, IV or V, or, iron which is present in oxidation state II, III or IV, X is a coordinating or bridging radical, n and m are each independently of the other an integer having a value of from 1 to 8, p is an integer having a value of from 0 to 32, z is the charge of the metal complex, Y is a counter-ion, q=z/(charge Y), and ligand L is a compound of formula (3)

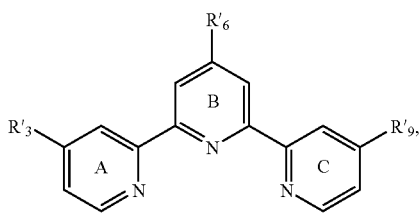

wherein $R'_6$ is cyano; halogen; nitro; —$COOR_{12}$ or —$SO_3R_{12}$; —$SR_{13}$, —$SO_2R_{13}$ or —$OR_{13}$; —$N(R_{13})$—$(CH_2)_{1-6}$$NR_{14}R_{15}$; —$N(R_{13})$—$(CH_2)_{1-6}$—$N^{\oplus}R_{14}R_{15}R_{16}$; —$N(R_{13})$—$N$—$R_{14}R_{15}$ or —$N(R_{13})$—$N^{\oplus}R_{14}R_{15}R_{16}$, wherein $R_{12}$ is in each case hydrogen, a cation, $C_1$-$C_{12}$alkyl, or phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, where the amino groups may be quaternized, phenyl, phenoxy or by naphthoxy;

$R_{13}$ is in each case hydrogen, $C_1$-$C_{12}$alkyl, or phenyl unsubstituted or substituted as indicated above;

and $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form a pyrrolidine, piperidine, morpholine or azepane ring which is unsubstituted or substituted by at least one unsubstituted $C_1$-$C_4$alkyl and/or substituted $C_1$-$C_4$alkyl;

or a radical

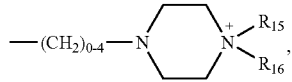

wherein $R_{15}$ and $R_{16}$ are as defined above; and $R'_3$ and $R'_9$ are as defined above for $R'_6$ or are hydrogen, $C_1$-$C_{12}$alkyl, or phenyl unsubstituted or substituted as indicated above, with the proviso that (i) at least one of the substituents $R'_3$, $R'_6$ and $R'_9$ contains a quaternized nitrogen atom which is not directly bonded to one of the three pyridine rings A, B or C

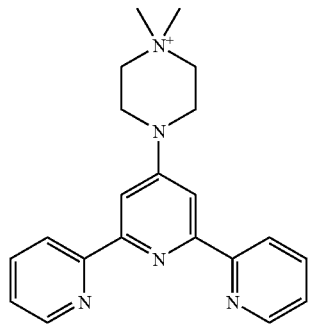

3. A washing, cleaning, disinfecting or bleaching agent, comprising
   I) 0-50% A) of an anionic surfactant and/or B) of a nonionic surfactant,
   II) 0-70% C) of a builder substance,
   III) 1-99% D) of a peroxide, and
   IV) E) a metal complex compound of formula (1a) according to claim 2 in an amount which, in the liquor, gives a concentration of 0.5-50 mg/litre of liquor when from 0.5 to 20 g/litre of the washing, cleaning, disinfecting and bleaching agent are added to the liquor,
   the percentages in each case being percentages by weight, based on the total weight of the agent.

4. A method according to claim 2, wherein X is $CH_3CN$, $H_2O$, $F^-$, $Cl^-$, $Br^-$, $HOO^-$, $O_2^{2-}$, $R_{17}COO^-$, $R_{17}O^-$, $LMeO^-$ or $LMeOO^-$ wherein $R_{17}$ is hydrogen, $-SO_3C_1$-$C_4$alkyl, or unsubstituted or substituted $C_1$-$C_{18}$alkyl or aryl.

5. A method according to claim 2, wherein Y is $R_{17}COO^-$, $ClO_4^{13}$, $BF_4^-$, $PF_6^-$, $R_{17}SO_3^-$, $R_{17}SO_4^-$, $SO_4^{2-}$, $NO_3^-$, $F^-$, $Cl^-$, $Br^-$, $I^-$, citrate, tartrate or oxalate, wherein $R_{17}$ is hydrogen or unsubstituted or substituted $C_1$-$C_{18}$alkyl or aryl.

6. A method according to claim 2, wherein n is an integer having a value of from 1 to 4.

7. A method according to claim 2, wherein m is an integer having a value of 1 or 2.

8. A method according to claim 2, wherein p is an integer having a value of from 0 to 4.

9. A method according to claim 2, wherein z is an integer having a value of from 8− to 8+.

10. A method according to claim 2, wherein $R_6'$ is

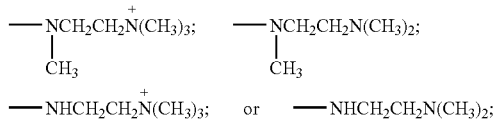

and $R_3'$ and $R_9'$ are as defined above for $R_6'$ or are hydrogen.

11. A method according to claim 2, wherein $R'_3$, $R'_6$ and $R'_9$ are each independently of the others cyano; nitro; $-COOR_{12}$ or $-SO_3R_{12}$, wherein $R_{12}$ is in each case hydrogen, a cation, $C_1$-$C_4$alkyl or phenyl; $-SR_{13}$, $-SO_2R_{13}$ or $-OR_{13}$ wherein $R_{13}$ is in each case hydrogen, $C_1$-$C_4$alkyl or phenyl; N-mono- or N,N-di-$C_1$-$C_4$alkyl-$N^{\oplus}R_{14}R_{15}R_{16}$, unsubstituted or substituted by hydroxy in the alkyl moiety, wherein $R_{14}$, $R_{15}$ and $R_{16}$ are each independently of the others hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form a pyrrolidine, piperidine, morpholine or azepane ring unsubstituted or substituted by at least one $C_1$-$C_4$alkyl or by at least one unsubstituted $C_1$-$C_4$alkyl and/or substituted $C_1$-$C_4$alkyl; N-mono- or N,N-di-$C_1$-$C_4$alkyl-$NR_{14}R_{15}$ unsubstituted or substituted by hydroxy in the alkyl moiety, wherein $R_{14}$ and $R_{15}$ can have the meanings indicated above, or a radical

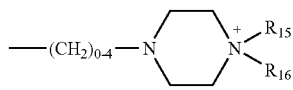

wherein $R_{15}$ and $R_{16}$ have the meanings indicated above, and the ring may be substituted, wherein $R'_3$ and $R'_9$ can also be hydrogen.

12. A method according to claim 2, wherein $R_6'$ is hydroxy.

13. A method according to claim 2, wherein a metal complex compound of formula (1a) is used in a washing, cleaning, disinfecting or bleaching agent.

14. A method according to claim 13, wherein a metal complex compound of formula (1a) is formed in situ in the washing, cleaning, disinfecting or bleaching agent.

15. A method according to claim 2, wherein a metal complex compound of formula (1a) is used together with a peroxy compound for the bleaching of spots or stains on textile material or for the prevention of the redeposition of migrating dyes in the context of washing process or for the cleaning of hard surfaces.

16. A method according to claim 2, wherein a metal complex compound of formula (1a) is used as a catalyst for reactions with a peroxy compound for bleaching in the context of paper-making.

17. A method according to claim 2, wherein a metal complex compound of formula (1a) is used as a catalyst for wastewater treatment.

18. A method according to claim 2, wherein a metal complex compound of formula (1a) is used as a catalyst for the deliginification of cellulose.

19. A method according to claim 2, wherein mixtures of manganese complexes of the formula (1a) with iron complexes of the formula (1a) are used for preventing the redeposition of migrating dyes and at the same time bleaching of spots or stains on textile material.

20. A method according to claim 2, wherein mixtures of manganese complexes of the formula (1a) with iron complexes which correspond to formula (1a) but contain no quaternized nitrogen atoms, are used.

* * * * *